United States Patent [19]
Nakanishi et al.

[11] Patent Number: 5,612,208
[45] Date of Patent: Mar. 18, 1997

[54] ASCORBATE OXIDASE, GENE ENCODING THE SAME, PROCESS FOR PRODUCING THE SAME, AND REAGENT COMPOSITION USING THE SAME

[75] Inventors: Yuji Nakanishi, Aichi; Hitoshi Amano; Shotaro Yamaguchi, both of Ibaraki, all of Japan

[73] Assignee: Amano Pharmaceutical Co., Ltd., Aichi, Japan

[21] Appl. No.: 439,114

[22] Filed: May 11, 1995

[30] Foreign Application Priority Data

May 11, 1994 [JP] Japan .................................. 6-123113

[51] Int. Cl.$^6$ .......................... C12N 9/02; C12N 15/53; C12Q 1/26; A23J 1/00
[52] U.S. Cl. ..................... 435/189; 426/541; 426/656; 435/25; 435/28; 435/252.3; 435/254.11; 435/172.3; 435/320.1; 435/254.21; 435/254.5; 435/254.3; 435/325; 536/23.2; 935/14
[58] Field of Search ............................. 435/189, 25, 28, 435/240.2, 252.3, 254.11, 240.4, 254.21, 254.5, 254.3, 320.1, 172.3; 536/23.2; 935/14; 426/541, 656

[56] References Cited

FOREIGN PATENT DOCUMENTS

0442781A2   8/1991   European Pat. Off. .

OTHER PUBLICATIONS

Ward, Jim, *The Enzymatic Oxidation of Ascorbic Acid in the Slime Mold, Physarum Polycephalum*, Plant Physiology, vol. 30, 1955, Botanical Lab., Univ. of Pennsylvania, Philadelphia, PA pp. 58–67.
Ohkawa et al., *Primary Structure of Cucumber (Cucumis sativus) Ascorbate Oxidase Deduced from cDNA Sequence: Homology with Blue Copper Proteins and Tissue–Specific Expression*, Proceedings of the National Academy of Sciences of USA, vol. 86, No. 4, pp. 1105–1430, Feb. 1989.
Abstract, Derwent Publication, Section Ch, Week 9416, JP-A-06-078-766, Mar. 22, 1994.

*Primary Examiner*—Dian C. Jacobson
*Assistant Examiner*—Nashaat T. Nashed
*Attorney, Agent, or Firm*—Sughrue, Mion, Zinn, Macpeak & Seas

[57] ABSTRACT

The present invention provides a novel ascorbate oxidase (ASOD) which catalyzes oxidation reaction of L-ascorbic acid with molecular oxygen to form L-dehydroascorbic acid and hydrogen peroxide, a process for producing the ascorbate oxidase comprising using a microorganism belonging to the genus Eupenicillium, a gene encoding ASOD, a transformant containing such a gene, a process for producing ASOD using such a transformant, and a reagent composition comprising ASOD, such as a reagent composition for examination, a food additive, and a reagent composition in the fields of food and clinical examination. The ascorbate oxidase has excellent stability particularly in a liquid state.

11 Claims, 13 Drawing Sheets

E: EcoRI
H: HindIII
K: KpnI
S: SalI
P: PstI
Ec: Eco47III
B: BstEII
Sa: SacI

H: HindIII
K: KpnI
S: SalI

ASCORBATE OXIDASE, GENE ENCODING THE SAME, PROCESS FOR PRODUCING THE SAME, AND REAGENT COMPOSITION USING THE SAME

FIELD OF THE INVENTION

This invention relates to a novel enzyme catalyzing oxidation of L-ascorbic acid. More particularly, the present invention relates to a novel L-ascorbate oxidase (hereinafter abbreviated as ASOD) which has extremely excellent stability and which catalyzes the reaction between L-ascorbic acid and molecular oxygen to form L-dehydroascorbic acid and hydrogen peroxide. In addition, the present invention relates to a process for producing ASOD using a microorganism, a gene encoding ASOD, a transformant containing such a gene, a process for producing ASOD using such a transformant, and a reagent composition comprising ASOD, such as a reagent composition for assays, a food additive, and a reagent composition in the fields of food and clinical examination.

BACKGROUND OF THE INVENTION

Known enzymes catalyzing oxidation of L-ascorbic acid include ascorbate oxidase (hereinafter abbreviated as ASO), which acts on ascorbic acid to form L-dehydroascorbic acid and water, and laccase, which are classified by the International Union of Biochemistry (IUB) as EC 1.10.3.3 and EC 1.10.3.2, respectively.

The above-mentioned ASO is known to be distributed in plants and has been isolated from pumpkins (M. H. Lee and C. R. Dawson, *J. Biol. Chem.*, Vol. 248, p. 6596 (1973)) and cucumbers (T. Nakamura, N. Makino and Y. Ogura, *J. Biochem.*, Vol. 64, p. 189 (1968)).

Also, ASO has been isolated from microorganisms, such as the hyphae of *Myrothecium verrucaria* (G. A. White and R. M. Krupka, Arch. *Biochem. Biphys.*, Vol. 110, p. 448 (1965)), and the spores of *Myrothecium verrucaria* (Funaki, et al., *Nihon Eiyo Shokuryo Gakkaishi*, Vol. 40, p. 47 (1987)), and cells of *Aerobacter aerogenes* (W. A. Volk and J. L. Larssen, *Biochem. Biophys.* Acta., Vol. 67, p. 576 (1963)), and the culture of Acremonium sp. HI-25 (S. Murao et al., *Biosci. Biotechnol. Biochem.*, Vol. 56, p. 847 (1992)).

The ASO species have been used widely in the fields of foods and clinical examination. In the field of foods, for example, ASO is used in combination with ascorbic acid for deoxidation, etc. of foodstuffs or for quality improvement of processed marine foodstuffs.

In the field of clinical examination, ASO is used for preventing the effect of ascorbic acid which strongly interferes with peroxidase-catalyzed coupled color-developing reactions between hydrogen peroxide and a chromogen. While the ascorbic acid level in serum is usually not higher than 1 mg/dl, generally giving rise to little problems, the ascorbic acid level is high in urine, etc. or even in blood when a large quantity of ascorbic acid is administered through infusion, thereby possibly influencing examination systems.

The influences of ascorbic acid can be excluded by (1) alkali treatment, (2) treatment with a copper ion or an iron ion, (3) periodic acid treatment or (4) ASO treatment. Usually, treatment (4) is used wherein ASO is added to a reagent for clinical examination.

In addition to the above-described ASO, an enzyme derived from *Physarum polycephalum* which acts on ascorbic acid to form hydrogen peroxide is known (*Plant physiology*, Vol. 30, p. 58 (1955)). However, detailed characteristics of this enzyme have not been studied.

In recent years, ascorbate oxidase derived from organisms of the genus Trichoderma or Mortierella, which has similar activity, i.e. act on ascorbic acid to form hydrogen peroxide, has been reported(JP-A-6-209770; the term "JP-A" as used herein means an "unexamined published Japanese patent application").

Of the above-described enzymes that act on ascorbic acid, a plant-derived ASO gene, which catalyzes a reaction to form L-dehydroascorbic acid and water, has been cloned (J. Ohkawa et al., *Proc. Natl. Acad. Sci. USA*, Vol. 86, p 1239 (1989)).

However, there are no reports regarding cloning of an ASO gene derived from microorganisms or an ASO gene of ASOD which catalyzes a reaction to form L-dehydroascorbic acid and hydrogen peroxide.

In recent years, many clinical diagnostic kits and reagents are provided not as lyophilized preparations but as liquid preparations. While the quality of liquid reagents is regarded to be guaranteed for about 1 year when preserved at 10° C., the quality of a reagent depends primarily on the stability of the various enzymes used in the liquid reagents. In this connection, the above-described ASO from plant or microorganism origin has insufficient stability for use in liquid reagents.

SUMMARY OF THE INVENTION

Ascorbate oxidase derived from *Physarum polycephalum* or from organisms of the genus Trichoderma or Mortierella, which catalyzes a reaction forming L-dehydroascorbic acid and hydrogen peroxide from ascorbic acid, is not satisfactory in terms of stability in a liquid, and thus does not solve a problem in the art of having a stable reagent which compensates for the unwanted presence of ascorbic acid in a sample.

The present inventors have intensively sought for a novel ascorbate oxidase in the natural world and, in particular, extensively searched for novel ascorbate oxidase enzymes of microbial origin. In the course of their study the present inventors found that a certain strain belonging to the genus Eupenicillium isolated from soil produces an extremely stable enzyme (ASOD) in the culture filtrate, which catalyzes the reaction of oxidizing ascorbic acid to form L-dehydroascorbic acid and hydrogen peroxide, a mechanism which is different from that when conventional ASO is used. Further, the present inventors established a process for producing the novel ASOD on an industrial scale, isolated and purified ASOD, and elucidated the properties and activities of ASOD. Furthermore, the present inventors have established a method for producing the novel ASOD on a large scale utilizing genetic engineering.

Thus, the present inventors cloned the gene encoding ASOD from chromosomal DNA derived from the strain belonging to the genus Eupenicillium; constructed a plasmid comprising such a gene and a DNA region which promotes expression of such a gene; produced a transformant containing such a plasmid; and established a process to produce ASOD by culturing such a transformant.

Moreover, in view of the extremely excellent stability of the present enzyme, the present inventors extensively studied the use of ASOD, such as in a liquid reagent.

The present invention has been completed based on these findings.

The oxidation reaction of ascorbic acid catalyzed by ASOD of the present invention is represented by reaction scheme (I):

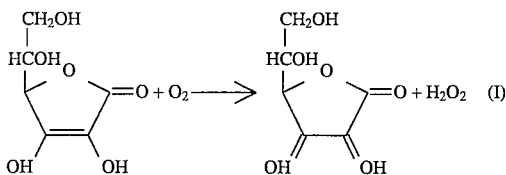

That is, the reaction catalyzed by ASOD is similar to the reaction catalyzed by the enzyme derived from *Physarum polycephalum* or from organisms of the genus Trichoderma or Mortierella, and is clearly distinguished from the reaction catalyzed by the conventional ASO.

The first object of the present invention is to provide a novel ASOD with excellent stability and which acts on L-ascorbic acid to form L-dehydroascorbic acid and hydrogen peroxide.

The second object of the present invention is to provide a process for producing the ASOD.

The third object of the present invention is to provide a gene encoding the ASOD.

The fourth object of the present invention is to provide a transformant containing a recombinant DNA comprising a gene encoding the ASOD and a DNA region which promotes expression of the gene.

The fifth object of the present invention is to provide a process for producing the ASOD, which comprises culturing a transformant containing a recombinant DNA comprising a gene encoding the ASOD and a DNA region which promotes expression of the gene, and harvesting the ASOD from the culture.

The sixth object of the present invention is to provide a reagent composition comprising the ASOD.

The seventh object of the present invention is to provide a food additive comprising the ASOD.

The eighth object of the present invention is to provide a reagent composition comprising the ASOD for measuring L-ascorbic acid in a sample.

Other objects of the present invention will be evident to the artisan, and particularly will be made apparent on a reading of the present application.

Specifically, the present invention provides:

(1) a novel ascorbate oxidase catalyzing a reaction between one molecule of L-ascorbic acid and one molecule of molecular oxygen to form one molecule of L-dehydroascorbic acid and one molecule of hydrogen peroxide, which acts on L-ascorbic acid and does not substantially act on araboascorbic acid, has an optimum pH of around pH 6, is stable at a pH of from about 3 to 8 when treated at 37° C. for 16 hours, has an optimum temperature of around 37° C., is stable at a temperature up to about 50° C. when treated at pH 6.8 for 16 hours, has residual activity of at least 50% when preserved as a solution at 37° C. for 1 month, and is not substantially inhibited by sodium azide, (2) a novel ascorbate oxidase obtained from a strain belonging to the genus Eupenicillium and catalyzing an oxidation reaction of L-ascorbic acid to form hydrogen peroxide and dehydroascorbic acid, (3) a novel ascorbate oxidase which is obtained from a strain belonging to the genus Eupenicillium, which acts on L-ascorbic acid to form L-dehydroascorbic acid and hydrogen peroxide, does not substantially act on D-araboascorbic acid, has an optimum pH of about 6, is stable at a pH of from about 3 to 8 when treated at 37° C. for 16 hours, has an optimum temperature around 37° C., is stable at a temperature up to about 50° C. when treated at pH 6.8 for 16 hours, has residual activity of at least 50% when preserved as a solution at 37° C. for 1 month, and is not substantially inhibited by sodium azide, (4) a process for producing an ascorbate oxidase comprising culturing a strain belonging to the genus Eupenicillium to produce an ascorbate oxidase and harvesting the ascorbate oxidase from the culture filtrate, (5) a gene encoding ascorbate oxidase which is a DNA fragment included in the region shown by the arrow in the restriction enzyme map of FIG. 6 and which has a base sequence encoding the N-terminal amino acid sequence represented by SEQ ID NO:1, (6) a gene encoding ascorbate oxidase which is a DNA fragment included in the region shown by the arrow in the restriction enzyme map of FIG. 6 and which has base sequences encoding amino acid sequences represented by SEQ ID NO:1, SEQ ID NO:2, SEQ ID NO:3, and SEQ ID NO:4, (7) a process for producing ascorbate oxidase, which comprises:

culturing a transformant containing a recombined DNA comprising a gene encoding ascorbate oxidase, which is a DNA fragment included in the region shown by the arrow in the restriction enzyme map of FIG. 6 and which has a N-terminal amino acid sequence represented by SEQ ID NO:1., and a DNA region which promotes expression of the gene; and harvesting the ascorbate oxidase from the culture, (8) a process for producing ascorbate oxidase, which comprises:

culturing a transformant containing a recombinant DNA comprising a gene encoding ascorbate oxidase, which is a DNA fragment included in the region shown by the arrow in the restriction enzyme map of FIG. 6 and which has base sequences encoding amino acid sequences represented by SEQ ID NO:1, SEQ ID NO:2, SEQ ID NO:3, and SEQ ID NO:4 and a DNA region which promotes expression of the gene; and harvesting the ascorbate oxidase from the culture, (9) a gene encoding ascorbate oxidase which is a cDNA fragment shown in the restriction enzyme map of FIG. 7 and which has a base sequence encoding N-terminal amino acid sequence represented by SEQ ID NO:1,

(10) a gene encoding ascorbate oxidase which is a cDNA fragment shown in the restriction enzyme map of FIG. 7 and which has base sequences encoding amino acid sequences represented by SEQ ID NO:1, SEQ ID NO:2, SEQ ID NO:3, and SEQ ID NO:4,

(11) a process for producing ascorbate oxidase, which comprises:

culturing a transformant containing a recombined DNA comprising a gene encoding ascorbate oxidase, which is a cDNA fragment shown in the restriction enzyme map of FIG. 7 and which has a N-terminal amino acid sequence represented by SEQ ID NO:1., and a DNA region which promotes expression of the gene; and harvesting the ascorbate oxidase from the culture. (12) a process for producing ascorbate oxidase, which comprises:

culturing a transformant containing a recombinant DNA comprising a gene encoding ascorbate oxidase, which is a cDNA fragment shown in the restriction enzyme map of FIG. 7 and which has base sequences encoding amino acid sequences represented by SEQ ID NO:1, SEQ ID NO:2, SEQ ID NO:3, and SEQ ID NO:4, and a DNA region which promotes expression of the gene; and harvesting the ascorbate oxidase from the culture,

(13) a reagent composition comprising an ascorbate oxidase catalyzing a reaction between L-ascorbic acid and molecular oxygen to form L-dehydroascorbic acid and hydrogen peroxide, which has residual activity of at least 50% when preserved as a solution at 37° C. for 1 month,

(14) a reagent composition comprising an ascorbate oxidase obtained from a strain belonging to the genus Eupenicillium, which has residual activity of at least 50% when preserved as a solution at 37° C. for 1 month,

(15) a food additive comprising an ascorbate oxidase catalyzing a reaction between L-ascorbic acid and molecular oxygen to form L-dehydroascorbic acid and hydrogen peroxide, which has residual activity of at least 50% when preserved as a solution at 37° C. for 1 month,

(16) a food additive comprising an ascorbate oxidase obtained from a strain belonging to the genus Eupenicillium, which has residual activity of at least 50% when preserved as a solution at 37° C. for 1 month, and

(17) a reagent composition for measuring L-ascorbic acid comprising an ascorbate oxidase catalyzing a reaction between L-ascorbic acid and molecular oxygen to form L-dehydroascorbic acid and hydrogen peroxide, which has residual activity of at least 50% when preserved as a solution at 37° C. for 1 month.

DETAILED DESCRIPTION OF THE INVENTION

Figure 1:
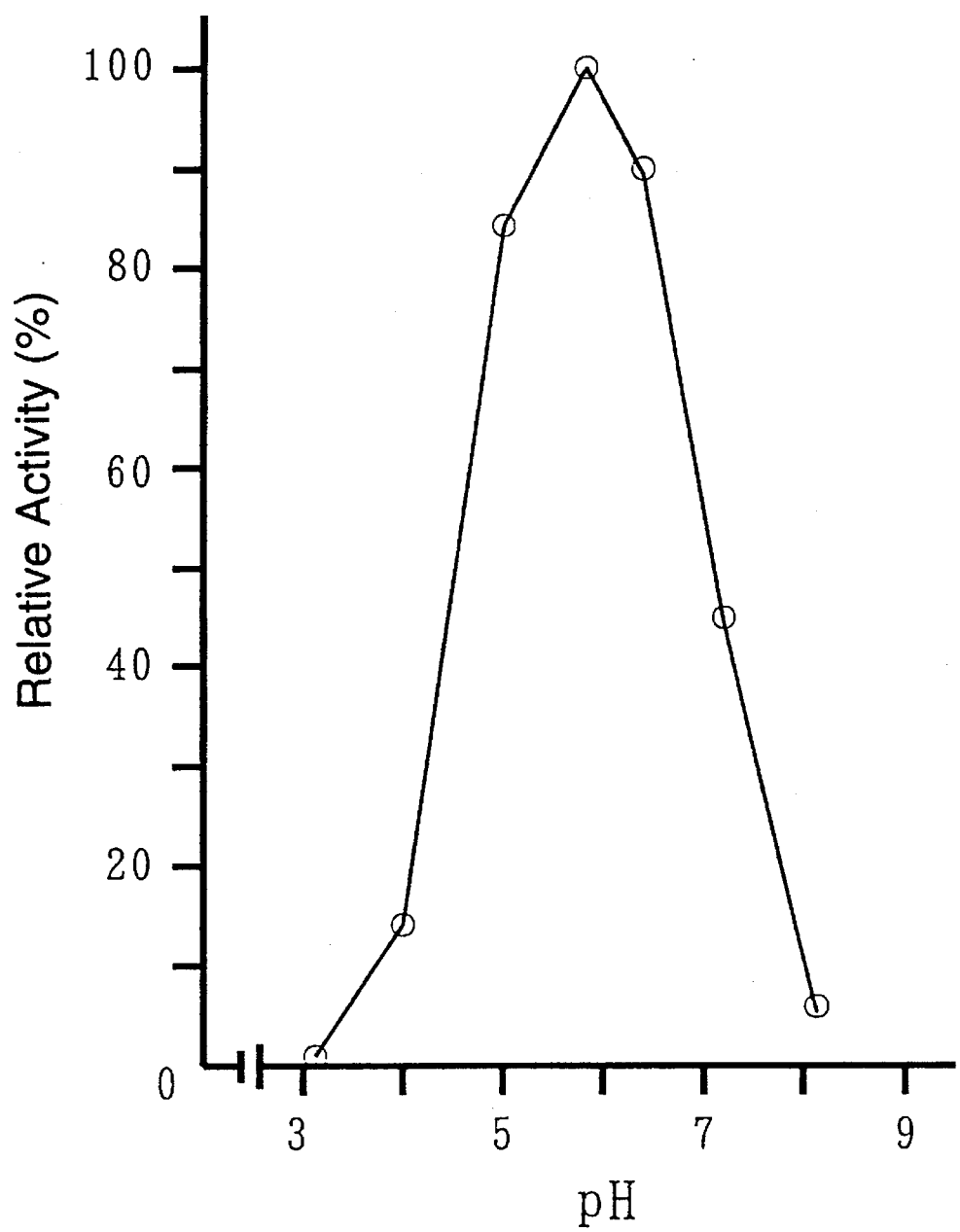
FIG. 1 is a graph of ASOD activity vs. pH, which shows an optimum pH of ASOD.

Hereinafter, the present invention will be described in greater detail.

The present inventors have intensively sought a microorganism as a source of a novel ascorbate oxidase and found that a certain strain belonging to the genus Eupenicillium isolated from soil is capable of producing such a novel ascorbate oxidase.

The strain isolated by the inventors was classified by the microbiological properties thereof based on K. B. Raper & C. Thom, *A Manual of the Penicillia*. As a result, it was identified as *Eupenicillium brefeldianum* and designated *Eupenicillium brefeldianum* APC-9315.

The microbiological properties of *E. brefeldianum* APC-9315 are described below.

(1) Growth

On a malt-agar medium, growth is relatively rapid and produces coarse, white and wooly hyphae to a height of 1 to 2 mm. Meanwhile the hyphae become visually vague and form a large number of ascocarps in close contact with the substrate. Colonies are flat and yellow to ocher. The reverse of the colonies is pale brown. On Czapek's agar medium, growth is slow, and colonies radially develop with a white dense mycelial tuft on the surface thereof, which meanwhile becomes felt-like. The periphery of the colonies is wavy, and brown asci densely gather there. The reverse of the colonies is deep brown, and rhizomorphs clearly appear and become more noticeable at 40° C.. On MY40-agar medium, the mycelial tuft is thick and carpet-like, and the reverse is deep brown. On oatmeal-agar medium, a number of powder-like ascocarps are formed, and the periphery of the colonies assumes a red color.

(2) Morphology

Ascocarp: cleistothecial; superficial; flesh-colored; spherical to ellipsoidal; diameter: 80 to 150 (200) μm; peridium; knit-like; hard.

Ascus: diameter: 6 to 8 μm; nearly spherical to egg-shaped; 8 spores; prototunicate.

Ascospore: colorless; spherical to egg-shaped; short needle-like projections over the entire surface.

chlamydospore: spherical to ellipsoidal; diameter: 4 to 6 μm

Conidiophore: 10 to 100×2 to 2 μm

Penicillus: *monoverticillus*; very rare

Phialide: 8×3 μm; mostly one or two

Conidium: spherical to nearly spherical; diameter: 2 to 3 μm; smooth surface; loose and entangled chains; length: 50 to 150 μm (3) Physiological Properties:

Casein decomposition:
+litmus milk (digestion)

Growth temperature:
14° to 40° C. (optimum: 37° C.)

Growth pH: 2.5 to 10.3 (optimum: 4.5 to 6.5)

Utilization of nitrogen:
well utilizes peptone, urea, ammonium secondary phosphate, sodium nitrate, and ammonium citrate; utilizes ammonium sulfate and ammonium chloride.

Utilization of carbon:
well utilizes many sugars such as glucose, starch and salicin; metabolism of mannitol and inulin is slightly inferior.

*Eupenicillium brefeldianum* APC-9315 has been deposited since Mar. 24, 1995 with the National Institute of Bioscience and Human-Technology, Agency of Industrial Science and Technology, MITI, 1-3, Higashi 1-chome, Tsukuba-shi, Ibaraki-ken 305, Japan and has been assigned accession number FERM BP-5053 under the Budapest Treaty.

As a result of investigations, it was confirmed that strains other than *Eupenicillium brefeldianum* which belong to the genus Eupenicillium are a source of ASOD. Examples of the strains other than *Eupenicillium brefeldianum* which belong to the genus Eupenicillium and which produce ASOD include *E. javanicum* IFO 31735, *E. alutaceum* IFO 31728, and E. erubescens IFO 31734. The ASOD activity of these strains is shown in Table 1. As is shown in the Table, *E. brefeldianum* APC-9315 newly screened from soil by the present inventors produces a high amount of ASOD.

TABLE 1

| Microorganism | Activity (unit/ml) |
| --- | --- |
| E. javanicum IFO 31735 | 0.019 |
| E. alutaceum IFO 31728 | 0.007 |
| E. erubescens IFO 31734 | 0.017 |
| E. brefeldianum APC-9315 | 0.250 |

Culturing of a microorganism belonging to the genus Eupenicillium for the production of ASOD may be by either liquid culture or solid culture, but preferably by liquid culture. Liquid culture can be carried out as follows.

Any culture medium may be used as long as the ASOD-producing microorganism can grow. For example, media containing carbon sources, such as glucose, sucrose, glycerin, dextrin, molasses, and organic acids; nitrogen sources, such as ammonium sulfate, ammonium carbonate, ammonium phosphate, ammonium acetate, peptone, yeast extract, corn steep liquor, casein hydrolyzate, and meat extract; and inorganic salts, such as potassium salts, magnesium salts, sodium salts, phosphates, manganese salts, iron salts, and zinc salts, may be employed.

The culturing is conducted at a pH usually of about 3 to 9, preferably about 5.5 to 6.5, at a temperature usually of about 10° to 50° C., preferably about 25° to 37° C., for a period of 1 to 20 days, preferably 3 to 12 days, under aerobic conditions, for example, by shake culture or aerobic submerged culture using a jar fermentor.

The solid culturing may be carried out as follows. Any solid culture medium may be used as long as the ASOD-producing microorganism can grow. For example, wheat bran, rice, soy bean, corn, paddy straw, wheat straw, and the like may be employed alone or as a mixture of two or more. Inorganic salts such as potassium salts, magnesium salts, sodium salts, phosphates, manganese salts, iron salts, and zinc salts, may be added.

The water content of the culturing medium is controlled to, for example, 50 to 300%, preferably 80 to 120%, and the culturing is usually conducted at a temperature of from about 10° to 50° C., preferably from about 25° to 40° C., for a period of 1 to 30 days, preferably 3 to 12 days.

As the bulk of ASOD was secreted into medium, the resulting culture was filtered to remove the microbial cells, or the solid culture is extracted with water or buffer to solubilize ASOD, and from the resulting filtrate or extract is isolated ASOD in a conventional manner to obtain the ASOD according to the present invention.

Isolation and purification of ASOD from the culture filtrate obtained by liquid culture or the extract obtained by solid culture can be performed in a usual manner by ammonium sulfate precipitation, alcohol precipitation, chromatography using ion-exchange resins, gel permeation chromatography, chromatography using hydroxylapatite-adsorbed resins, or the like technique to obtain purified ASOD.

The properties of the novel purified ASOD obtained by liquid culture of *Eupenicillium brefeldianum* APC-9315 are described below in greater detail.

(1) Optimum pH

FIG. 1 shows the relative activity of ASOD obtained by reaction in Britton-Robinson's buffer having a pH varying from 3.0 to 8.0 at a temperature of 30° C. for 10 minutes. The ASOD has an optimum pH of around pH 6.

(2) Optimum Temperature

Figure 2:
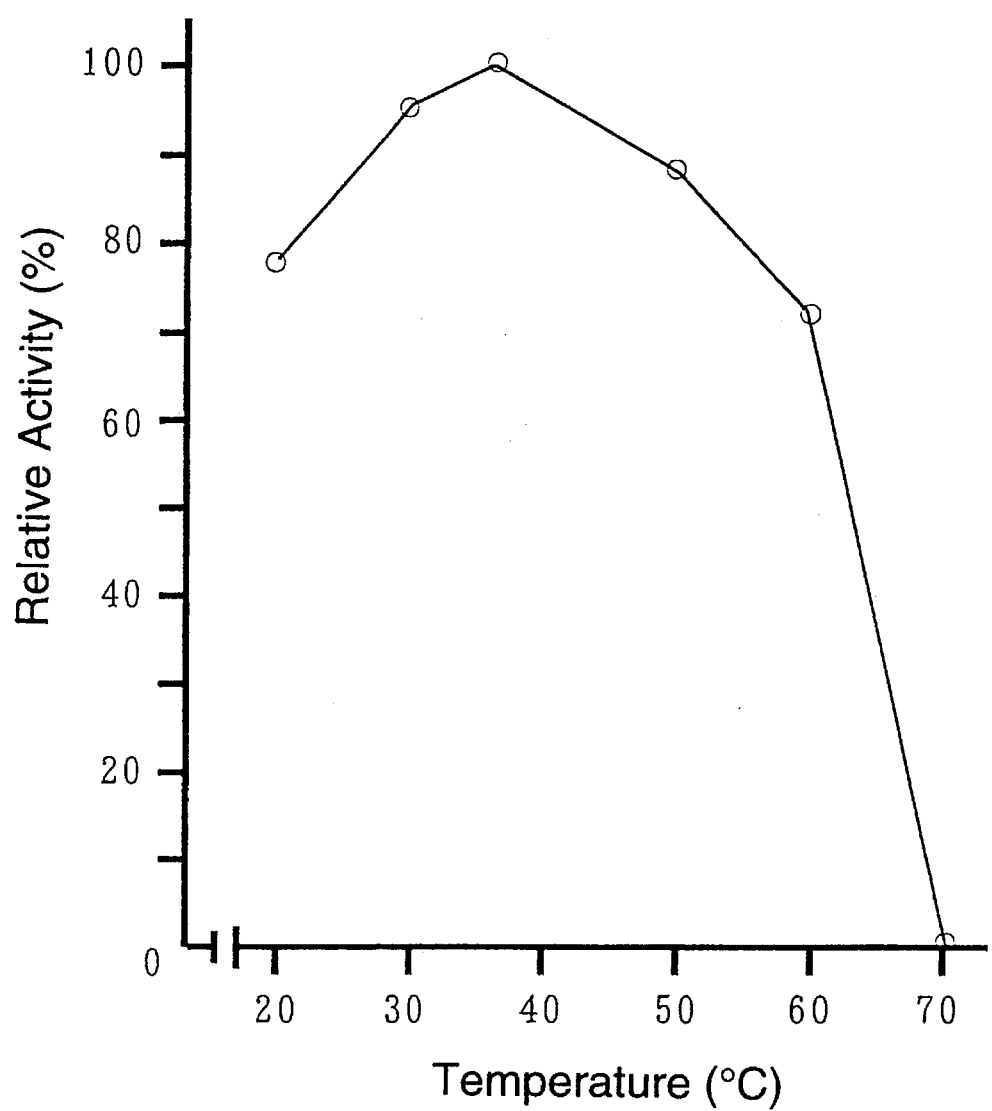
FIG. 2 is a graph of ASOD activity vs. temperature, which shows an optimum temperature of ASOD.

FIG. 2 shows the relative activity of ASOD obtained by reaction in a 100 mM potassium phosphate buffer (pH: 5.5) at varying temperatures for 10 minutes. At pH 5.5, the ASOD has an optimum temperature of around 37° C.

(3) pH Stability

Figure 3:
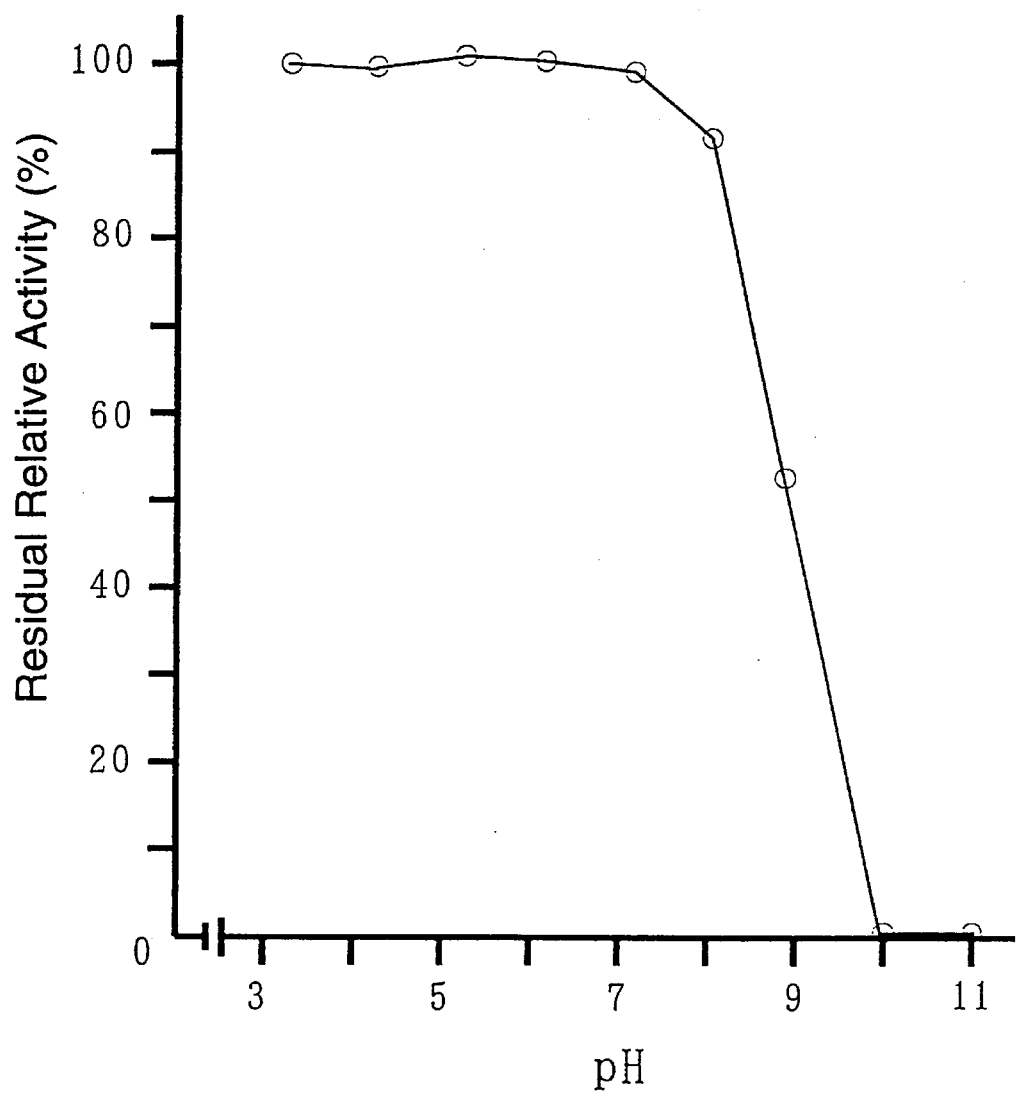
FIG. 3 is a graph of ASOD residual activity vs. pH, which shows the pH stability of ASOD.

FIG. 3 shows the relative residual activity of ASOD after incubation in Britton-Robinson's buffer under different pH conditions at 37° C. for 16 hours. The ASOD is stable in a pH range of from about 3 to 8 under the above-mentioned conditions.

(4) Temperature Stability

Figure 4:
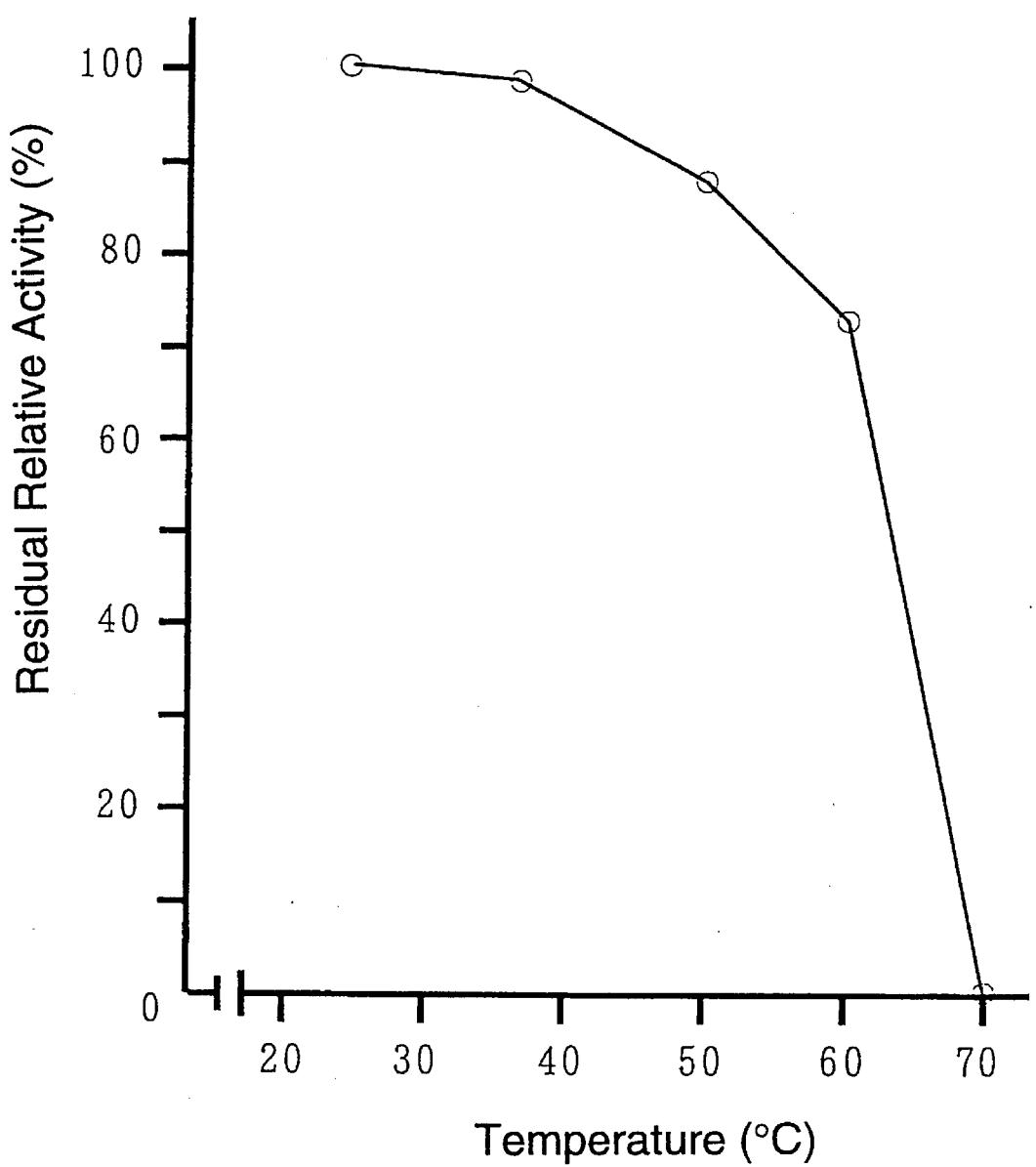
FIG. 4 is a graph of ASOD residual activity vs. temperature, which shows temperature stability of ASOD.

FIG. 4 shows the relative residual activity of ASOD after incubation in 100 mM PIPES (piperazine-N,N'-bis(2-ethanesulfonic acid)) buffer (pH: 6.8) at varying temperatures for 16 hours. The ASOD is stable at about 50° C. or lower under the above-mentioned conditions.

(5) Molecular Weight

About 135,000 (as measured by gel permeation chromatography using Sephadex G-200).

(6) Inhibitor

The relative residual activity of ASOD after incubation with various inhibitors at 37° C. for 2 hours. The ASOD is not substantially inhibited by sodium azide, dithiothreitol (DTT), or a diethyldithiocarbamate (chelating agent) and is inhibited partially by monoiodoacetic acid (MIA).

Influences of various metal ions on the activity of ASOD are shown in Table 2.

TABLE 2

| Metal Salt | Concentration (mM) | Relative Residual Activity (%) |
| --- | --- | --- |
| control (no addition) | — | 100 |
| NaCl | 100 | 98 |
| $MgCl_2$ | 5 | 98 |
| $CaCl_2$ | 5 | 102 |
| $MnCl_2$ | 5 | 98 |
| $ZnCl_2$ | 5 | 100 |
| $CoCl_2$ | 5 | 96 |
| $FeCl_2$ | 5 | 68 |
| $FeCl_3$ | 5 | 7 |
| $NiCl_2$ | 5 | 101 |
| $BaCl_2$ | 5 | 98 |
| $CuCl_2$ | 5 | 100 |

(8) Michaelis Constant (Km) for L-Ascorbic Acid $4.9 \times 10^{-4}$ M (by the spectrophotometry method)

(9) Substrate Specificity ASOD reacts with L-ascorbic acid and does not react with D-araboascorbic acid. Neither does ASOD react with various ascorbic acid derivatives, such as L-ascorbic acid phosphate magnesium salt, L-ascorbic acid 6-palmitate, and L-ascorbic acid-2,6-dipalmitate. ASOD does not use hydroquinone or pyrogallol as a substrate.

(10) Preservation Stability

Figure 5:
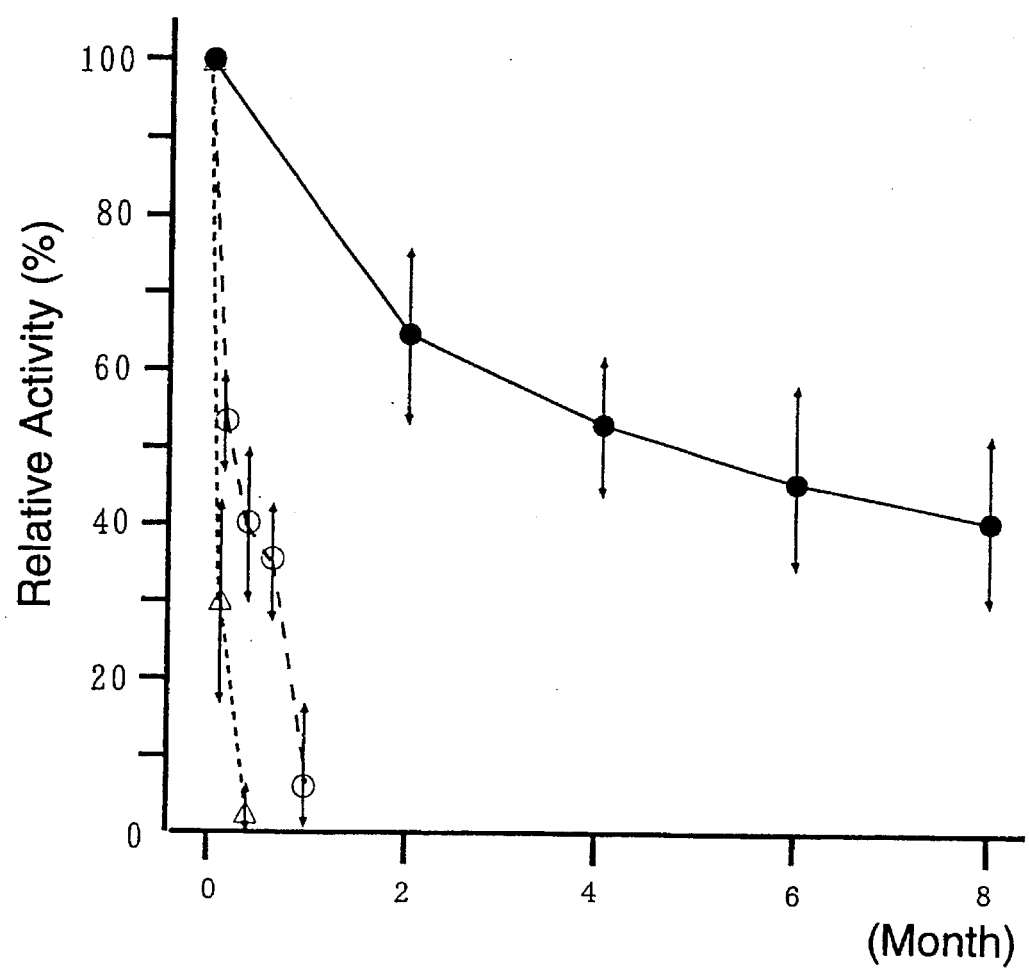
FIG. 5 is a graph of ASOD residual activity during long-term preservation, which shows the preservation stability of ASOD. Filled circles indicate the ASOD of the present invention, hollow circles indicate ASO of Acremonium sp. HI-25, and hollow triangle indicate ASO of cucumber.

FIG. 5 shows the relative residual activity of ASOD preserved at 37° C. in a dissolved state in a 50 mM PIPES buffer (pH: 6.5) (containing 0.02M dehydroacetic acid and 1 mM EDTA). For comparison, the results of ASO species derived from Acremonium sp. HI-25 (produced by Asahi Kasei Kogyo Kabushiki Kaisya) and cucumber (produced by Amano Pharmaceutical Co., Ltd.) are also shown in FIG. 5.

It is seen that ASOD of the present invention exhibits very satisfactory stability when preserved under the above-described conditions. For example, the residual activity of the ASOD after a 1 month storage under the above conditions is at least 50%, showing excellent stability as compared with the two ASO enzymes compared. That is, the ASO of Acremonium sp. HI-25 has a residual activity as low as about 5% after a 1 month storage, meaning nearly complete inactivation, and that of cucumber was substantially completely inactivated following storage of only several days.

Thus, the ASOD of the present invention exhibits markedly excellent stability in solution without the aid of any special stabilizers.

The aforesaid properties of the ASOD of the present invention are compared with known ascorbate oxidase enzymes (such as those derived from Acremonium sp. HI-25, derived from spores of *Myrothecium verrucaria*, described in JP-A-6-209770, and derived from cucumber in Table 3).

nucleotide and those including inosine may be used [S. Yamaguchi et. al., Gene, Vol. 103, p. 61 (1991)].

Using the resulting DNA fragment as a probe, the ASOD gene can be obtained as a DNA fragment from the genome DNA library of *Eupenicillium brefeldianum* APC-9315 or the like. Similarly, a DNA fragment containing the ASOD gene may be obtained from the genome DNA library of other microorganisms belonging to the genus Eupenicillium, such as the strains recited in Table 1. The DNA may contain various base sequence including intron (intervening sequence). One skilled in the art can easily select the existence or inexistence of intron, the sequence of intron and the position at which the intron is inserted according to the various factors regarding the gene expression system such as the type of the host cell.

TABLE 3

| | ASOD | | Known ASO | | |
|---|---|---|---|---|---|
| Origin | *Eupenicillium brefeldianum* APC-9315 | *Acremonium* sp. HI-25 | Spores of *Myrothecium verrucaria* | Microorganism of the Genus *Trichoderma* or *Mortierella* | Cucumber |
| Sources of Data | | Biosci. Biotechnol. Biochem., 56 (6), 847–852 (1992) & JP-A-3-236766 | Nihon Eiyo-Shokuryo Gakkaishi, 40, (1), 47–51 (1987) | JP-A-6-209770 | J. Biochem., 64 189 (1968) |
| Molecular Weight | about 135,000 (GPC) | 80,000 (GPC) 76,000 (SDS-PAGE) | 380,000 (GPC) | about 416,000 (GPC) | 132,000 (GPC) |
| Km (L-Ascorbate) | $4.9 \times 10^{-4}$M | — | $3.0 \times 10^{-3}$M | $7.0 \times 10^{-4}$M | $2.5 \times 10^{-4}$M |
| Optimum pH | around 6.0 | 3.5–4.5 | 6.0–7.0 | about 4.0 | 5.6 |
| Optimum Temp. | about 40° C. | 45° C. | 30° C. | about 30° C. | 30° C. |
| pH Stability | about 3–8 (37° C. × 16 hrs) | 4–11 (4° C. × 17 hrs) | — | 3–8 (25° C. × 19 hrs) | 7–10 (25° C. × 17 hrs) |
| Temp. Stability | About 50° C. or lower (pH: 6.8, 16 hrs) | 60° C. or lower (pH: 8.0, 30 min.) | 40° C. or lower | 55° C. (pH: 8.0, 30 min. | 40° C. or lower (pH: 8.0, 30 min.) |
| Sodium Azide | uninhibited | inhibited | uninhibited | — | inhibited |
| Diethyldithio-carbamate | uninhibited | uninhibited | inhibited | — | inhibited |
| Monoiodoacetic acid | inhibited (50%) | — | — | uninhibited | — |

*"GPC" in the Table stands for gel permeation chromatography

The ASOD may be purified from strains other than *Eupenicillium brefeldianum* APC-9315 (*E. javanicum* IFO 31735, *E. alutaceum* IFO 31728, and *E. erubescens* IFO 31734). The ASOD species obtained from these strains were found to have the same properties as that of *E. brefeldianum* APC-9315 with respect to, for example, optimum pH, optimum temperature, pH stability, temperature stability, molecular weight, susceptibility to known inhibitors, influence of metal ion, Michaelis Constant (Km) for L-Ascorbic Acid, substrate specificity, and preservation stability.

Obtaining and using gene encoding the ASOD of the present invention now will be described in detail.

Cloning the desired gene may be carried out by employing the conventional methods such as the hybridization screening using as a probe an oligonucleotide deduced from the partial amino acid sequence of the ASOD, the immunoscreening using an antibody, and the like.

Alternatively, oligonucleotides are designed and synthesized based on the amino acid sequences of the different two parts in the N-terminal region of the purified protein or the internal peptide obtained by chemical or enzymatic digestion of the protein, and a DNA fragment can be obtained by the PCR (Polymerase Chain Reaction) method using these oligonucleotides as the sense primer and the antisense primer. As the synthetic oligonucleotide, a mixed oligo- After cloning of the genomic sequence, a corresponding cDNA can be obtained by screening a cDNA library with a probe obtained from the genomic clone, or obtained by the PCR method. As the probe for PCR, an oligonucleotide designed and synthesized based on, for example, the base sequence just upstream of the initiation codon and just downstream of the termination codon of the ASOD gene coding region.

A plasmid comprising a gene encoding the ASOD and a DNA region which promotes expression of the gene may be obtained by, for example, integrating the above-described DNA fragment in a plasmid containing a DNA region which promotes expression of the gene. As a DNA region which promotes expression of the gene, any DNA sequence can be employed as long as it is capable of promoting expression of the ASOD gene in the host microorganism used.

The transformant containing the above-described plasmid according to the present invention, which can produce ASOD in the cell or secrete ASOD outside of the cell, may be obtained by introducing the above-described plasmid in a host microorganism such as filamentous fungi, yeast, etc. As the host microorganism, any microorganism can be used as long as it is capable of producing a recombinant ASOD, and examples thereof include microorganisms of the genera Eupenicillium, Penicillium, Aspergillus, and Saccharomyces, the bacterial strains such as *E. coli* and Bacillus sp., and mammalian cells.

The method for culturing the above-mentioned transformant containing a recombinant DNA comprising a gene encoding the ASOD and a DNA region which promotes expression of the gene according to the present invention and the method for producing ASOD from that culture can be carried out by, for example, the method used for obtaining naturally occurring ASOD from an organism of the genus Eupenicillium as taught herein.

That is, the present invention makes it possible to obtain ASOD from a culture which is obtained by culturing a microorganism containing a recombinant DNA comprising a gene encoding the ASOD and a DNA region which promotes expression of the gene.

The reagent composition for clinical examination as referred to in the present invention is a reagent composition which can be used for assaying biological components using a peroxidase-catalyzed coupled reaction between hydrogen peroxide and a chromogen. In such an assay system, the adverse influences of L-ascorbic acid present in a sample can be avoided by using the ASOD of the present invention. While the ASOD of the present invention is applicable to various reagents for clinical examination, it is particularly suited in assays of various biological components conducted at about a neutral pH because the ASOD of the present invention has an optimum pH at about 7.

For example, the ASOD can be included in the measurement systems using an oxidative condensation reaction of hydrogen peroxide and a chromogen in the presence of peroxidase, such as in assays of cholesterol, neutral fats, free fatty acids, phospholipids, uric acid, creatinine, inorganic phosphorus, sialic acids, etc. The ASOD of the present invention is usually used in an amount of about 0.1 to 100 units per assay, but varying depending on the concentration of L-ascorbic acid present in a sample and the size of the reaction. For example, 0.5 to 10 units/assay, preferably 1 to 5 units/assay, of ASOD is used for a 0.4 ml-reaction system.

The ASOD of the present invention is far superior to known ASO enzyme with respect to stability in solution. When using conventional ASO, increased amount of ASO are required to compensate for the inactivation during storage, which has led to not only an increase of examination cost but increased liability to influences of impurities.

Further, the above-mentioned reagents for clinical examination often contain sodium azide as a preservative of the active ingredients in a reagent. Since the known ASO enzymes of plant origin or Acremonium sp. HI-25 origin are inhibited by sodium azide, additional manipulations are required to retain ASO activity as in using antiseptics. The novel ASOD of the present invention is not inhibited by sodium azide and hence is superior also in this aspect.

While the reaction catalyzed by the ASOD of the present invention produces hydrogen peroxide, the peroxide can be removed by a condensation reaction with 4-aminoantipyrine or a derivative thereof or a phenolic compound or an N,N-disubstituted aniline compound in the presence of peroxidase. The peroxide also can be decomposed by catalase.

Many current reagents for clinical diagnosis have a means for removing hydrogen peroxide, for example, a first reagent of two-reagent system is designed so as to remove intrinsic interfering substances such as hydrogen peroxide. Therefore, the production of hydrogen peroxide formed in the oxidation reaction by ASOD can be controlled so as not to adversely influence measurement of various biological components where hydrogen peroxide is an interfering substance.

The advantages of the novel ASOD according to the present invention over conventional ASO, i.e., very high storage stability, not inhibited by sodium azide, and an optimum pH in the vicinity of neutrality, make it possible to reduce the required amount of enzyme to be added to a reagent for clinical examination, which ultimately leads to reduction of cost and avoidance of influences of impurities.

In addition, conventional ASO has a catalytic activity reacting to a condensation reaction of 4-aminoantipyrine and a hydrogen donor, such as phenol. As a result, ASO increases the reaction amount in a reagent blank in an assay of a biological component using an oxidase/peroxidase detection system. The reagent blank in the assay using the ASOD of the present invention is lower than that observed with the conventional ASO of plant or microorganism origin and thus provides for greater sensitivity. From this point of view, the ASOD is suitably utilized for oxidase/peroxidase measurement systems.

The ASOD is also useful in foods. For example, ASOD of the present invention can be added to foodstuffs containing ample L-ascorbic acid or be added in combination with L-ascorbic acid or a salt thereof to those foodstuffs which contain no or insufficient L-ascorbic acid, whereby L-ascorbic acid is oxidized, and the oxygen in the food is thus consumed to prevent deterioration of the food.

When added to processed foodstuffs, such as processed livestock and fish meat products and fish-paste products, the combination of ASOD and L-ascorbic acid produces dehydroascorbic acid in the foods which improves the quality in the foods. That is, dehydroascorbic acid produced having a strong oxidizing power is capable of acting on SH groups of proteins in foods to form S-S bonds. According to this function, glutinosity and elasticity, which are important factors decisive of the quality of these kinds of foods, are improved.

For use in foods as described above, ASOD is added in an amount of not less than 0.001 unit, preferably 0.01 unit, per gram. Where L-ascorbic acid in a foodstuff is low, L-ascorbic acid or a salt thereof may be added to the foodstuff in an amount of 0.01 to 1.0% by weight.

On addition of ASOD to foods, hydrogen peroxide is produced in the foods but is decomposed during the course of food processing, such as in a heating step. If desired, hydrogen peroxide may be decomposed by using catalase, etc. Therefore, the production of hydrogen peroxide gives rise to no safety problems when adding ASOD to foods.

Unlike conventional ASO, ASOD of the present invention acts on L-ascorbic acid to catalyze a reaction of forming 1 mole of hydrogen peroxide from 1 mole of L-ascorbic acid. This catalyzing action of ASOD can be used for measuring the L-ascorbic acid concentration in a foodstuff or a biological sample, i.e., the L-ascorbic acid concentration in a sample can be assayed by measuring hydrogen peroxide production.

Measurement of hydrogen peroxide can be carried out by a method utilizing a condensation reaction of 4-aminoantipyrine and a hydrogen donor, e.g., phenol, in the presence of peroxidase; a method in which hydrogen peroxide is decomposed by the action of catalase in the presence of methanol, determining the amount of formaldehyde produced in a reaction with formaldehyde dehydrogenase; or a method using a hydrogen peroxide electrode.

In an ascorbic acid measurement system utilizing the reducing power of ascorbic acid, the ASOD can also be used in the blank reaction as is with conventional ASO.

In the present invention, the ASOD activity was determined as follows.

To 0.1 ml of a sample to be assayed is added 0.5 ml of 10 mM $Na_2HPO_4$ and 0.45 ml of 0.2M $KH_2PO_4$ containing 1 mM EDTA, and the mixture is mixed and preincubated at 30° C. for 5 minutes. To the mixture is added 0.05 ml of a 10 mM substrate solution of L-ascorbic acid in 0.001N HCl containing 1 mM EDTA, followed by incubation at 30° C. for 10 minutes. The reaction is stopped by addition of 3.0 ml of 0.2N HCl, and a reduction in absorbance at 245 nm is measured. The amount of ASOD in the sample which decomposes 1 μmol of L-ascorbic acid per 1 minute is taken as one unit.

The present invention will now be illustrated in greater detail with reference to Examples. The plasmids used in the Examples were used as examples. The plasmids used in the present invention are not limited to these plasmids and other plasmids may be used in the present invention as long as they can be used in the present invention. It should be understood that the present invention is not deemed to be limited the following Examples and changes and modifications usually made in the art can be applied.

EXAMPLE 1

Culturing of *E. brefeldianum* APC-9315

A medium (20 l; pH: 6.0) containing 2% (w/v) glycerol, 1% (w/v) polypeptone, 2% (w/v) fish extract (Wako Pure Chemical Industries), 0.2% (w/v) $K_2HPO_4$, 0.01% (w/v) $MgSO_4 \cdot 7H_2O$, and 0.001% (w/v) Adecanol LG126 (Asahi Denka Kogyo) was charged in a jar fermentor and sterilized at 121° C. for 30 minutes. Separately, *E. brefeldianum* APC-9315 (FERM BP-5053) had been shake-cultured in a 500 ml-volume Sakaguchi's flask at 37° C. for 3 days using the same medium. The above prepared sterilized medium was sterilely inoculated with 100 ml of the culture and cultivated at 37° C. for 6 days under aeration (10 l/min.) and agitation (200 rpm). The culture filtrate had an ASOD activity of 0.15 unit/ml.

EXAMPLE 2

Purification of ASOD

The culture obtained in Example 1 was filtered using Toyo Filter Paper No. 2 to recover 12 l of the culture filtrate. The culture filtrate was concentrated to 1 l using a module of ultrafiltration. To the concentrate was added cold ethanol in an amount 1.5 times as much as the volume of the concentrate, followed by stirring in a refrigerator overnight. The solid content was collected by centrifugal separation and dissolved in a 10 mM acetate buffer (pH: 5.0).

The solution was passed through a column packed with DEAE-Sepharose equilibrated with the above buffer, and the column was washed with the same buffer to collect the fraction which had not been adsorbed to DEAE-Sepharose. The fraction was then passed through a column packed with S-Sepharose equilibrated with 20 mM acetate buffer (pH: 4.4). After thoroughly washing the column with the same buffer, elution was carried out with linear gradient of sodium chloride (0 to 200 mM). The recovered active fraction was desalted and concentrated using a module of ultrafiltration and the concentrate was lyophilized to obtain a powder. The resulting ASOD powder had a specific activity of 1,495 units/mg-protein.

EXAMPLE 3

Identification of Enzyme Reaction Product and Stoichiometry

Ten units of the ASOD preparation obtained in Example 2 were added to a 20 mM acetate buffer (pH: 5.0), and L-ascorbic acid was added thereto to a final concentration of from 0 to 50 mM. The mixture was allowed to react thoroughly while stirring. A 50 μl aliquot of the resulting reaction mixture was mixed with 2.95 ml of a 100 mM phosphate buffer (pH: 7.0) containing 3 mM (final concentration, hereinafter the same) 4-aminoantipyrine, 1.1 mM phenol, 24 U horse radish peroxidase, and 0.02% Triton X-100, and the mixture was allowed to react at 37° C.. It was observed that 516 micromoles of hydrogen peroxide was produced with consumption of 501 micromoles of L-ascorbic acid.

Catalase was made to act on the thus produced hydrogen peroxide in the presence of methanol, and the resulting formaldehyde was determined using formaldehyde dehydrogenase. As a result, a quantitative relationship was observed between the consumption of L-ascorbic acid and the production of hydrogen peroxide.

The product in the reaction mixture was identified to be dehydroascorbic acid by HPLC, dinitrophenyl hydrazine colorimetry, and o-phenylenediamine fluorometry. The results of the fluorometry assay revealed production of 60.0 micromoles of dehydroascorbic acid with consumption of 61.0 micromoles of L-ascorbic acid.

The consumption of oxygen during the reaction was measured with an oxygen electrode. It was found as a result that 9.7 micromoles of oxygen had been consumed with consumption of 10 micromoles of L-ascorbic acid.

All these results made it clear that the ASOD of the present invention catalyzes a reaction in which 1 mole of L-ascorbic acid is oxidized with 1 mole of oxygen as a hydrogen acceptor to produce 1 mole of dehydroascorbic acid and 1 mole of hydrogen peroxide.

EXAMPLE 4

Culturing of *Eupenicillium javanicum* IFO 31735, *Eupenicillium alutaceum* IFO 31728 and *Eupenicillium erubescens* IFO 31734

Specific activities of ASOD enzymes obtained by culturing these strains in accordance with the procedure of Example 1 and purifying the thus produced enzymes in accordance with the procedure of Example 2 were found to be 1,356 units/mg protein, 1,631 units/mg protein and 1,567 units/mg protein, respectively. Each of these enzymes catalyzes a reaction in which 1 mole of L-ascorbic acid is oxidized using 1 mole of oxygen as a hydrogen receptor to form 1 mole of dehydroascorbic acid and 1 mole of hydrogen peroxide.

EXAMPLE 5

Cloning of ASOD gene (1) Preparation of cells

*Eupenicillium brefeldianum* APC-9315 (FERM BP-5053) was inoculated into a glycerol-polypeptone medium (2% glycerol, 3% polypeptone, 0.2% $KH_2PO_4$, 0.01% $MgSO_4 \cdot 7H_2O$, 0.001% Adecanol, pH 6.0) and cultured at 37° C. for 48 hours with aeration and agitation, and the resulting cells were recovered from the culture by filtration.

(2) Preparation of chromosomal DNA

A 4 g portion of the thus obtained wet cells were frozen in liquid nitrogen, transferred as such into a mortar containing liquid nitrogen and sea sand and then pulverized into a fine powder using a pestle.

The thus obtained powder was suspended in 6 ml of lysis buffer (150 mM EDTA.2Na, 50 mM Tris-HCl buffer (pH 8.0), 1% sarcosine) containing 3 mg of proteinase K, treated at 65° C. for 5 minutes and then subjected to centrifugation to recover the resulting supernatant.

This was mixed with 30 μl of RNase A (10 mg/ml), treated at 37° C. for 20 minutes to degrade RNA, extracted with 1 volume of phenol, 1 volume of phenol:chloroform (1:1) and 1 volume of chloroform:isoamyl alcohol (24:1) in that order and then subjected to ethanol precipitation to recover the thus formed precipitate, which was subsequently dissolved in 2 ml of TE buffer (150 mM EDTA. 2 Na, 50 mM Tris-HCl buffer, pH 8.0). This was further mixed with 2.2 ml of 20% polyethylene glycol 8000–2.5M NaCl, and the thus formed precipitate was collected by centrifugation to obtain 0.2 mg of chromosomal DNA which was subsequently dissolved in TE.

(3) Preparation of mRNA

Total RNA was obtained in accordance with the method of Chirgwin et al. (*Biochemistry*, Vol. 18, p. 5294 (1979)). That is, half of the powder obtained in the above step (2) was suspended in 20 ml of GTC solution (6M guanidine thio-isocyanate, 5 mM sodium citrate, 8.5% sarcosine, 0.1M β-mercaptoethanol) and centrifuged at 10,000×g for 15 minutes to remove cell disrupt and sea sand.

The thus obtained supernatant was layered over a solution of 5.7M cesium chloride in an ultracentrifugation tube and subjected to 18 hours of ultracentrifugation at 33,000 rpm and at 25° C.. The resulting precipitate was dissolved in water and mixed with 0.025 volume of 1N acetic acid and 0.5 volume of cold ethanol, and the thus formed precipitate was collected by centrifugation, dissolved in water and then centrifuged to remove impurities, thereby obtaining about 10 mg of total RNA. A 4 mg portion thereof was subjected to an Oligo(dT)cellulose-Span-Column Kit (manufactured by Pharmacia) to select and obtain 80 μg of a poly-A mRNA fraction.

(4) Preparation of gene library

The total DNA obtained in the above step (2) was digested with BglII. The thus digested DNA fragments were dephosphorylated using calf intestine alkaline phosphatase (manufactured by Boehringer) and ligated to the BamHI site of XDASHII (manufactured by Stratagene Co.) in accordance with the method of Frischauf et al. (*J. Mol. Biol.*, Vol. 170, pp. 827–842 (1987)).

The ligation mixture was subjected to in vitro packaging and transfected into *E. coli* XL1-Blue MRA(P2) (manufactured by Stratagene Co.). As a result, a library consisting of $3.8 \times 10^5$ independent clones was obtained.

(5) Determination of ASOD partial amino acid sequence

The purified ASOD protein obtained in Example 2 was treated with endoglycosidase H to remove sugar chains. The sugar chain-removed ASOD was subjected to SDS-polyacrylamide gel electrophoresis and then electrically blotted on a PVDF membrane (polyvinylidene difluoride membrane manufactured by Millipore Co.). Thereafter, an ASOD band stained with Coomassie Brilliant Blue R-250 was cut out to determine the N-terminal amino acid sequence (SEQ ID NO: 1) using an Edman method-based automatic amino acid sequence analyzer (manufactured by Applied Biosystems).

Next, the sugar chain-removed ASOD was digested with N-hydroxylamine in accordance with a known method [*Protein Primary Structure (New Biochemical Experimental Course Vol. 1)*, p. 92 (1990), The Japanese Biochemical Society; (written in Japanese)]. The resulting mixture of peptide fragments was blotted onto a PVDF membrane in the same manner as described above, and a band of a peptide (peptide D) stained with Coomassie Brilliant Blue R-250 was cut out to determine N-terminal amino acid sequence (SEQ ID NO: 2) of the peptide D in the same manner.

Next, the sugar chain-removed ASOD [3 mg/ml, 100 mM phosphate buffer (pH 8.0)]was mixed with lysyl endopeptidase (manufactured by Takara) and subjected to 18 hours of digestion at 37° C.. The digested products were purified by reverse phase HPLC method using a Puresil C18 column (manufactured by Waters Chromatography Co.). Peptides were eluted at a flow rate of 1.0 ml/min with a linear gradient of 0 to 80% acetonitrile in 0.05% trifluoroacetic acid.

A peptide which eluted at about 34 minutes of retention time (peptide L-34) and a peptide which eluted at about 39 minutes (peptide L-39) were separated to determine the respective N-terminal amino acid sequences (SEQ ID NO: 3 and SEQ ID NO: 4) by the Edman method.

(6) Synthesis of primer DNA for the PCR method

To be used as a PCR sense primer, a mixed oligonucleotide having the following sequence was synthesized based on the nucleotide sequence deduced from the 3 position proline to 10 position glycine of the N-terminal amino acid sequence of full-length ASOD protein determined in the above step (5).

(SEQ ID NO: 7)
```
5'-CCT GCI GCT GTI TAT AAT GGT GG-3'
    C   C       C   C   C
    A   A           A
    G   G           G
```
(I: Inosine)

In the same manner, a mixed oligonucleotide having the following sequences was synthesized as a PCR antisense primer, based on the nucleotide sequences deduced from the 6 position proline to the 13 position aspartic acid of the N-terminal amino acid sequence of the peptide D determined in the above step (5).

(SEQ ID NO: 8)
```
3'-GGT CGI ACC ATA TGI ACT GCI CT-5'
   C         G        T
   A
   G
```
(I: Inosine)

Each of the thus synthesized DNA fragments was dissolved in TE to a final concentration of 20 μM.

(7) Preparation of a partial DNA fragment containing the ASOD gene

A specified DNA region containing the ASOD gene was isolated and amplified by the PCR method and isolated (Saiki, R. F. et al., *Science*, Vol. 230, pp. 1350–1354 (1985); Mullis, K. B. and Faloona, F. A., *Methods in Enzymology*, Vol. 155, pp. 335–350 (1987)).

(a) Amplification of DNA fragment by the PCR method

The reaction was carried out using Gene Amp™ kit (manufactured by Perkin-Elmer Japan) and a DNA amplification apparatus purchased from the same manufacturer (DNA Thermal Cycler). The composition of the reaction solution is as follows.

|  |  | (final concentration) |
| --- | --- | --- |
| $H_2O$ | 62.5 μl |  |
| [10×] Reaction buffer | 10 μl | [1×] |
| dNTPs, Mix 1.25 mM | 16 μl | 200 μM |
| Sense primer | 5 μl | 4 μM |
| Antisense primer | 5 μl | 4 μM |
| Chromosomal DNA | 1 μl |  |
| AmpliTaq ™ DNA polymerase | 0.5 μl | 2.5 U/Test |
|  | 100 μl |  |

A 100 μl portion of the above reaction solution was mixed, followed by the addition of 100 μl of mineral oil (manufactured by Siena). Next, a tube containing the reaction solution was set in the DNA Thermal Cycler, and the reaction was carried out under the following conditions.

94° C. 45 seconds
45° C. 1 minute
72° C. 2 minutes

After 30 cycles of the reaction under these conditions, a final incubation was carried out at 72° C. for 5 minutes.

(b) Recovery of amplified DNA

After the final incubation, the mineral oil was removed, and the reaction solution was mixed with 100 μl of chloroform and subjected to 2 minutes of centrifugation (a centrifugation machine manufactured by Tomy Seiko) at 15,000 rpm to recover 100 μl of supernatant. A 5 μl portion of this was subjected to 1% agarose electrophoresis to check the size and quantity of the thus recovered DNA. As a result, it was confirmed that about 2 μg of a DNA fragment having a size of about 400 bp had been amplified.

The remaining 95 μl portion was subjected to 1% low melting point agarose electrophoresis, and a band corresponding to about 400 bp was cut out, the slice was dissolved at 65° C. and mixed with 1 volume of phenol. After centrifugation, the resulting aqueous layer was treated with phenol/chloroform and chloroform in that order, mixed with 0.1 volume of 3M sodium acetate and 2 volumes of ethanol and then allowed to stand for 15 minutes at –80° C.. This then was subjected to 10 minutes of centrifugation at 15,000 rpm and at 4° C., and the resulting precipitate was dissolved in 20 μl of TE. About 1 μg of the DNA fragment was recovered by this procedure.

The DNA fragment was treated with T4 DNA polymerase to form blunt ends at both termini thereof and then subcloned into the SmaI site of pUC19 to obtain plasmid pASO3. This double-stranded plasmid was purified with polyethylene glycol, denatured with alkali and then analyzed by the deoxynucleotide chain termination method using the Sequenase System (manufactured by USB) to determine 5'- and base sequences.

As a result, the 5'- and 3'-base sequences completely coincided with the base sequences encoding the 4 to 20 position amino acid sequence of mature ASOD and the 1 to 13 position amino acid sequence of the peptide D, respectively.

This fragment was used as a probe in the screening of a gene library for the isolation of a complete length genomic DNA clone.

(8) Isolation of phage containing ASOD gene

The 400 bp PCR product obtained in the above step (7)-(b) was labeled with [α-$^{32}$P]dCTP using the Multi Prime DNA Labeling System (manufactured by Amersham). Using this as a probe, phage containing ASOD gene were screened from a gene library constructed in the above step (4) consisting of 7.5×10$^4$ independent phage.

That is, plaques were transferred onto a nylon membrane, Hybond N$^+$ (manufactured by Amersham), and fixed with .alkali, and the resulting filter was hybridized with the labeled 400 bp DNA fragment.

As a result, 14 plaques hybridized with the probe. A total of 14 recombinant phage DNA isolated from these plaques were analyzed by restriction enzyme mapping and Southern blotting.

All of these phage commonly contained both an 18 kbp BglII and a 4.2 kbp EcoRI fragment which hybridize strongly with the 400 bp PCR product.

(9) Determination of base sequence of DNA fragment containing ASOD gene

Figure 6:
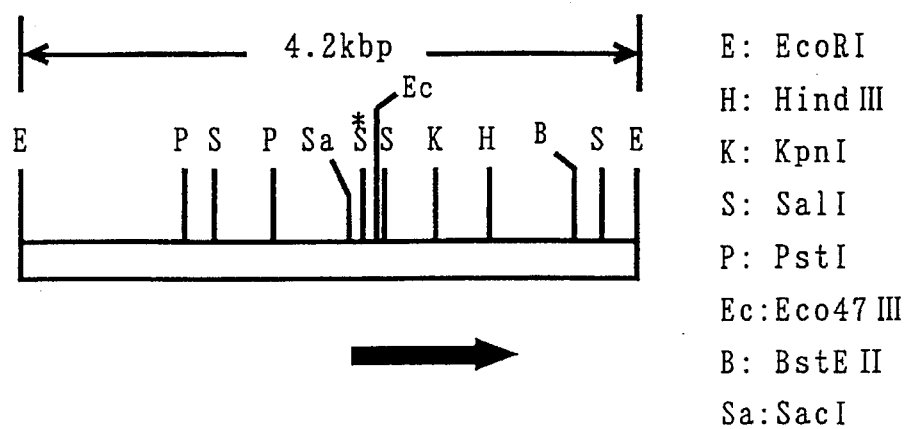
FIG. 6 is a restriction enzyme map of a DNA fragment including the ASOD gene.

The 4.2 kbp EcoRI fragment was subcloned into the EcoRI site of pUC19 to prepare plasmids pASO3 and pASOR3 in which the 4.2 kbp EcoRI fragment was inserted in reverse directions. A restriction enzyme map of the 4.2 kbp EcoRI fragment is shown in FIG. 6.

Several deletion plasmids were prepared from both of these plasmids using exonuclease III and horsebean nuclease, and their base sequences were determined in accordance with the procedure described in the above step (7)-(b). An amino acid sequence deduced from the thus determined base sequence completely contained the 20 residue amino acid sequence determined from the purified ASOD N-terminus, the 20 residue amino acid sequence of the peptide D and each of the 12 residue amino acid sequences of the peptides L-34 and L-39. The determined base sequence of downstream region from the SalI cut site marked with * in FIG. 6 was as shown in SEQ ID NO: 5. This indicates that the N-terminal amino acid of mature ASOD was Val which is encoded by the base sequence of this SalI cut site. The region of 18 amino acid residues which starts from Met and exists just upstream of the N-terminal Val of the mature ASOD is considered to be the prepro region. The arrow in the FIG. 6 indicates the DNA region encoding from this Met to the C-terminal amino acid of ASOD.

(10) Isolation of cDNA fragment (a) Synthesis of single-stranded cDNA for PCR template Single-stranded cDNA was prepared in 20 μl of the following reaction solution from the mRNA (1 μg) obtained in the above step (3).

20 mM; Tris-HCl buffer (pH 8.4)

2.5mM; Magnesium Chloride 50 mM; Potassium Chloride 0.1 μg/ml; BSA 5 mM; Dithiothreitol 0.5mM; dNTP Mixture 0.025 μg/ml; Oligo d(T)

10units RNase H$^-$ Reverse Rranscriptase (trade name, SuperScript™; manufactured by BRL)

(b) Amplification of cDNA by the PCR method

Using the single-stranded cDNA obtained in the above step (10)-(a), amplification was carried out by the PCR procedure described in (7)-(a). In this case, the following oligonucleotides were synthesized using a DNA synthesizer to be used as sense and antisense primers.

Sense primer (SEQ ID NO:9)

EX-1: 5'-ATT CTA GAC ATC ATG CGT TCC TAT ACT TTG-3'

Antisense primer (SEQ ID NO:10)

B-1: 3'-CGT TGG CTC ACA ACA ACT ATC CTA GGT G-5'

These nucleotide sequences were designed based on the sequence information obtained by determining the nucleotide sequences just upstream of the initiation codon and just downstream of the termination codon of the ASOD gene-encoding region in the 4.2 kbp EcoRI fragment.

Figure 7:
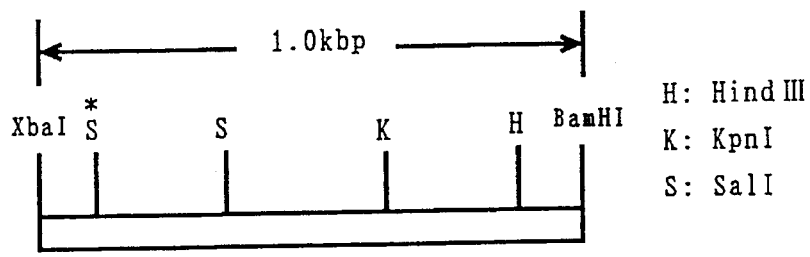
FIG. 7 is a restriction enzyme map of a cDNA fragment including the ASOD gene.

As the result of PCR, a cDNA fragment of about 1.0 kbp was obtained. This fragment was digested with XbaI and BamHI and subcloned into the XbaI/BamHI site of pUC19 to obtain pAXB1. The restriction enzyme map of this XbaI/BamHI fragment of about 1.0 kbp is shown in FIG. 7. The XbaI and BamHI sites at both sides are derived from the base sequence of the PCR primers used in the cDNA cloning. The base sequence of this DNA fragment was determined according to the method described in (7b). The base sequence from the initiation codon to the termination codon was in agreement with the base sequence of the gene except the intron sequence found near Eco47III site.

(11) Construction of ASOD expression cassette

Figure 8:
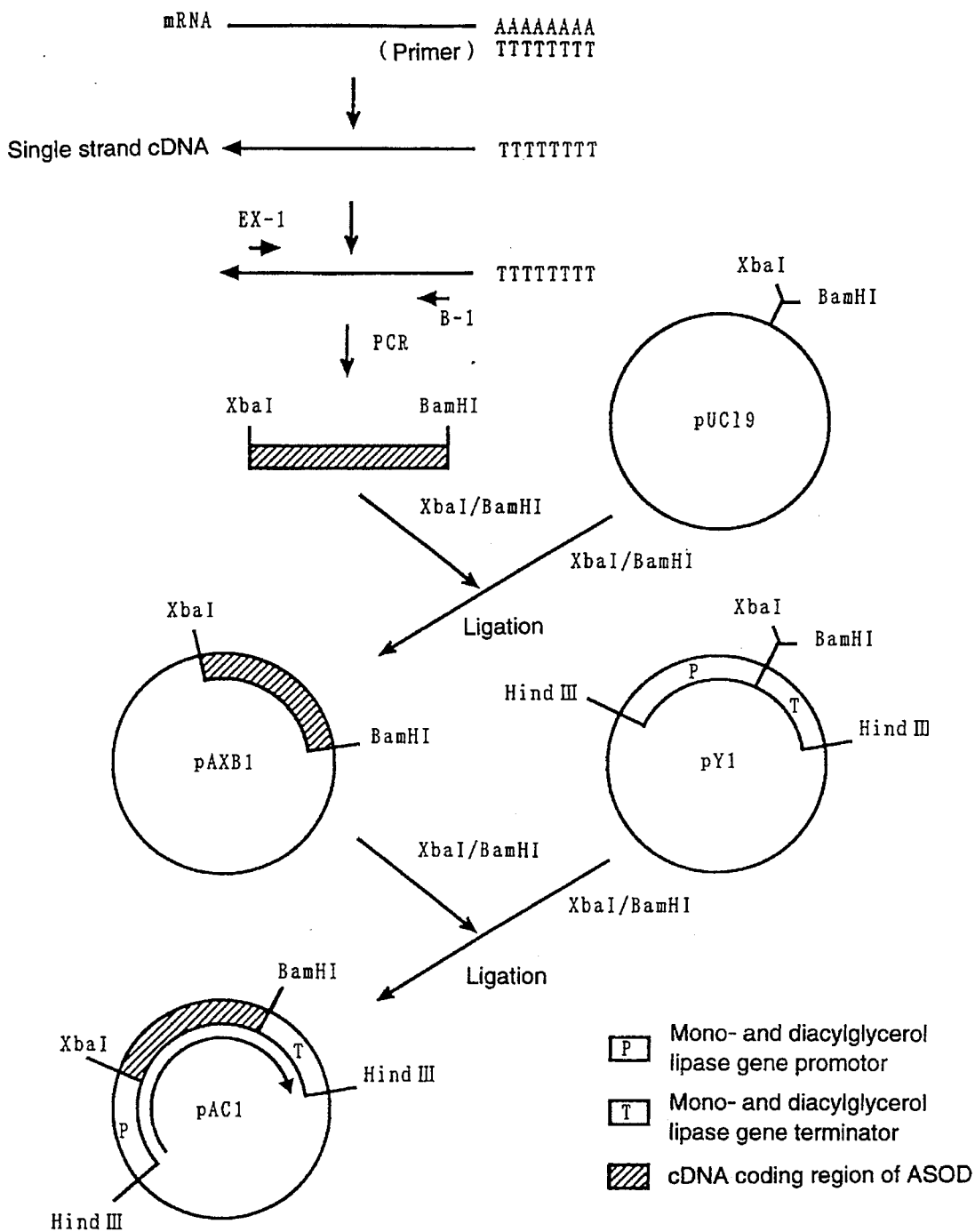
FIG. 8 shows a procedure for the construction of a recombinant plasmid pAC1.

The pAXB1 obtained in the above step (10) was digested with restriction enzymes XbaI and BamHI, and the mixture of digested fragments was subjected to 1% low melting point agarose electrophoresis to isolate and purify a DNA fragment of about 1.0 kbp. This DNA fragment was cloned into the XbaI/BamHI site of pY1 (JP-A-6-245777) to obtain pAC1 (cf. FIG. 8).

EXAMPLE 6

Expression of ASOD gene in *Saccharomyces cerevisiae*

Figure 9:
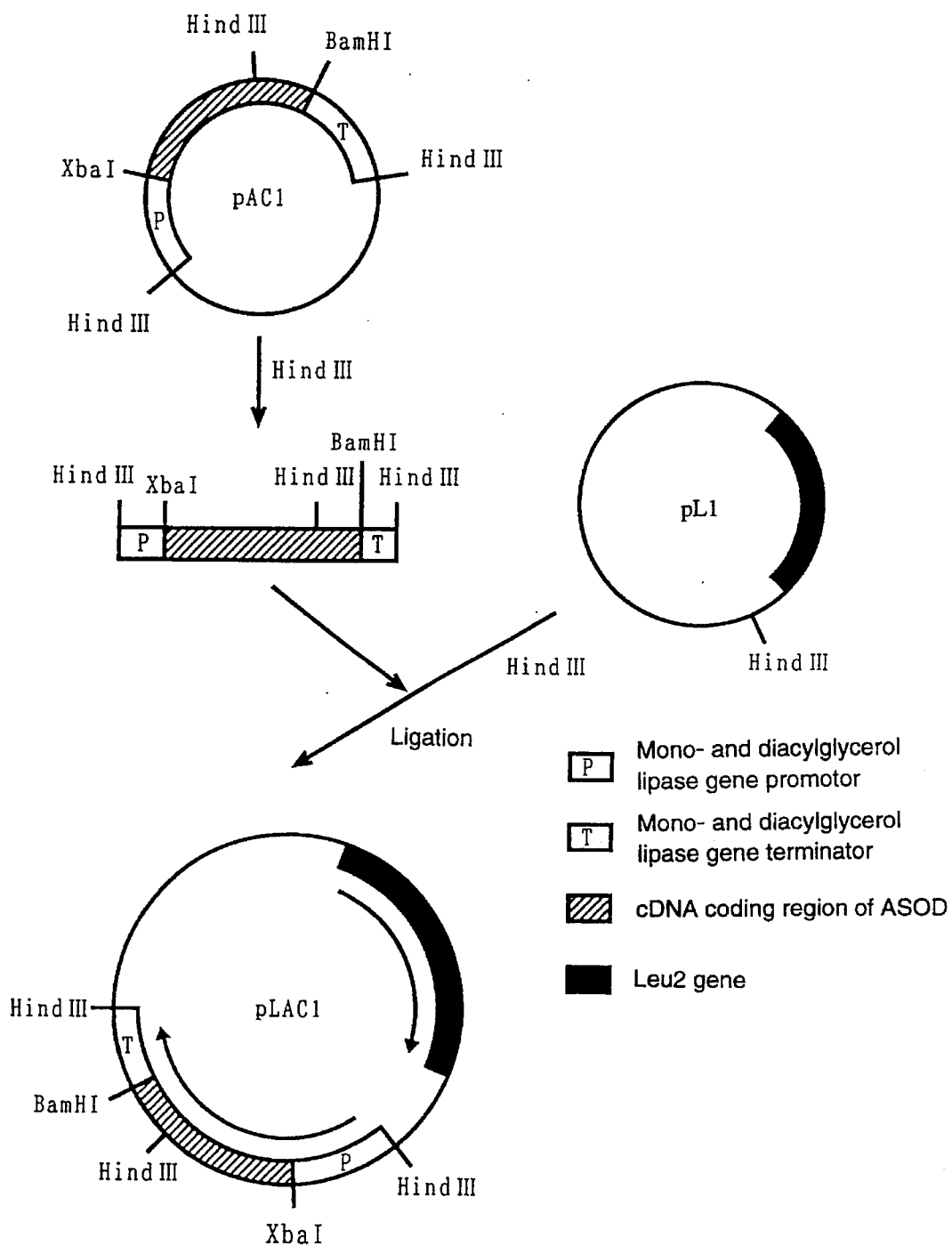
FIG. 9 shows a procedure for the construction of a recombinant plasmid pLAC1.

The pAC1 obtained in Example 5-(11) was partially digested with HindIII, and the mixture of digested fragments was subjected to 1% low melting point agarose electrophoresis to isolate and purify a DNA fragment of about 2.1 kbp as the ASOD expression cassette. This DNA fragment was linked to the HindIII site of a transformation plasmid pL1 (*Biosci. Biotech. Biochem.*, Vol. 56, pp. 315–319 (1992)) which contains the Leu2 gene which can be used as a selection marker in *Saccharomyces cerevisiae* (FIG. 9).

Using the thus obtained pLAC1, transformation of *Saccharomyces cerevisiae* SHY2 (ATCC 44770) was carried out in accordance with the method of Ito et al. (*J. Bacteriol.*, Vol. 153, pp. 163–168 (1983)). The resulting transformant was cultured in 50 ml of PYGal medium (2% galactose, 2% polypeptone, 1% yeast extract) at 30° C. for 3 days with shaking.

The ASOD activity in the culture supernatant thus obtained was measured at 0.3 U/ml. As a control, a transformant was isolated having only the selection marker gene-containing plasmid pL1 and cultured in the same manner. ASOD activity was not detected in the control.

When each culture filtrate of these two transformants was subjected to sugar chain removal in accordance with the procedure described in Example 5-(6) and analyzed by SDS-polyacrylamide gel electrophoresis and western blotting. From the western blotting analysis, an anti-ASOD rabbit antibody prepared using purified ASOD was used. As a result, a band of protein having the same molecular weight of native, deglycosylated ASOD was detected only in the case of the pLAC1 transformant and not the control, and this protein was confirmed to be capable of reacting with an anti-ASOD antibody.

EXAMPLE 7

Expression of ASOD gene in *Penicillium camembertii*

Figure 10:
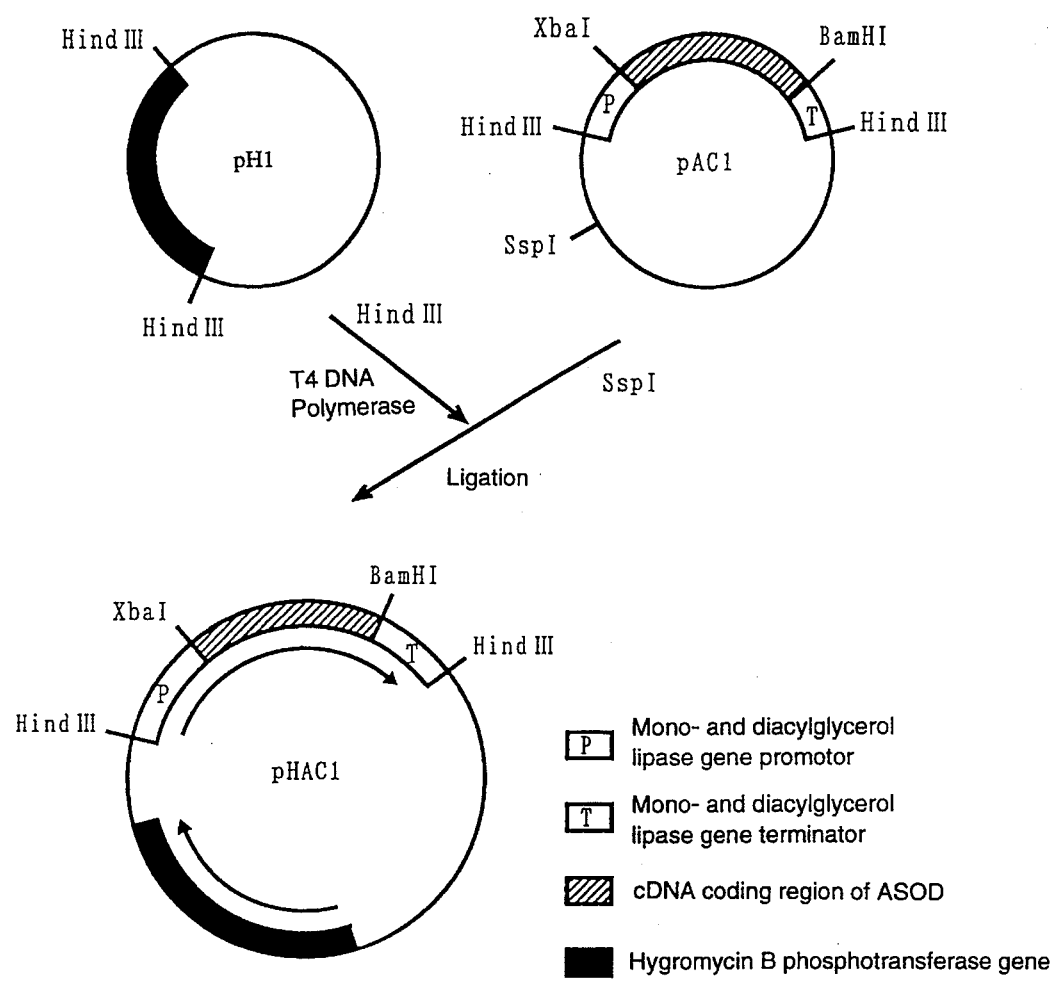
FIG. 10 shows a procedure for the construction of a recombinant plasmid pHAC1.

A transformation plasmid pH1 (produced in accordance with the procedure disclosed in JP-A-6-245776) having a hygromycin B resistance gene to be used as a selection marker for *Penicillium camembertii* was digested with HindIII, and the mixture of digested fragments was subjected to 1% low melting point agarose electrophoresis to isolate and purify a DNA fragment of about 2.2 kbp containing the hygromycin B resistance gene. The thus obtained DNA fragment was treated with T4 DNA polymerase to form blunt ends at both termini thereof and then cloned into the SspI restriction enzyme site of the recombinant plasmid pAC1 prepared in Example 5-(11) to obtain a plasmid pHAC1 (FIG. 10).

Using the thus obtained pHAC1, transformation of *Penicillium camembertii* was carried out in accordance with the method disclosed in JP-A-6-245776. A transformant grown on a selective medium was cultured in 100 ml of soybean oil medium (3% soybean oil, 0.5% yeast extract, 0.3% NaNO$_3$, 0.1% K$_2$HPO$_4$, 0.05% KCl, 0.05% MgSO$_4$.7H$_2$O, 0.001% FeSO$_4$.12H$_2$O) at 30° C. for 7 days with shaking.

The ASOD activity in the culture filtrate thus obtained was measured at 14.9 U/ml. As a control, a transformant was isolated using only the selection marker gene-containing plasmid pH1 and cultured in the same manner. ASOD activity was not detected in the control.

When each culture filtrate of these transformants was subjected to sugar chain removal in accordance with the procedure described in Example 5-(6) and analyzed by SDS-polyacrylamide gel electrophoresis and western blotting in the same manner as in Example 6, a band of protein having the same molecular weight of native, deglycosylated ASOD was detected only in the case of the pHAC1 transformant, and this protein was confirmed to be capable of reacting with an antiASOD antibody.

EXAMPLE 8

Expression of ASOD gene in *Aspergillus oryzae*

Figure 11:
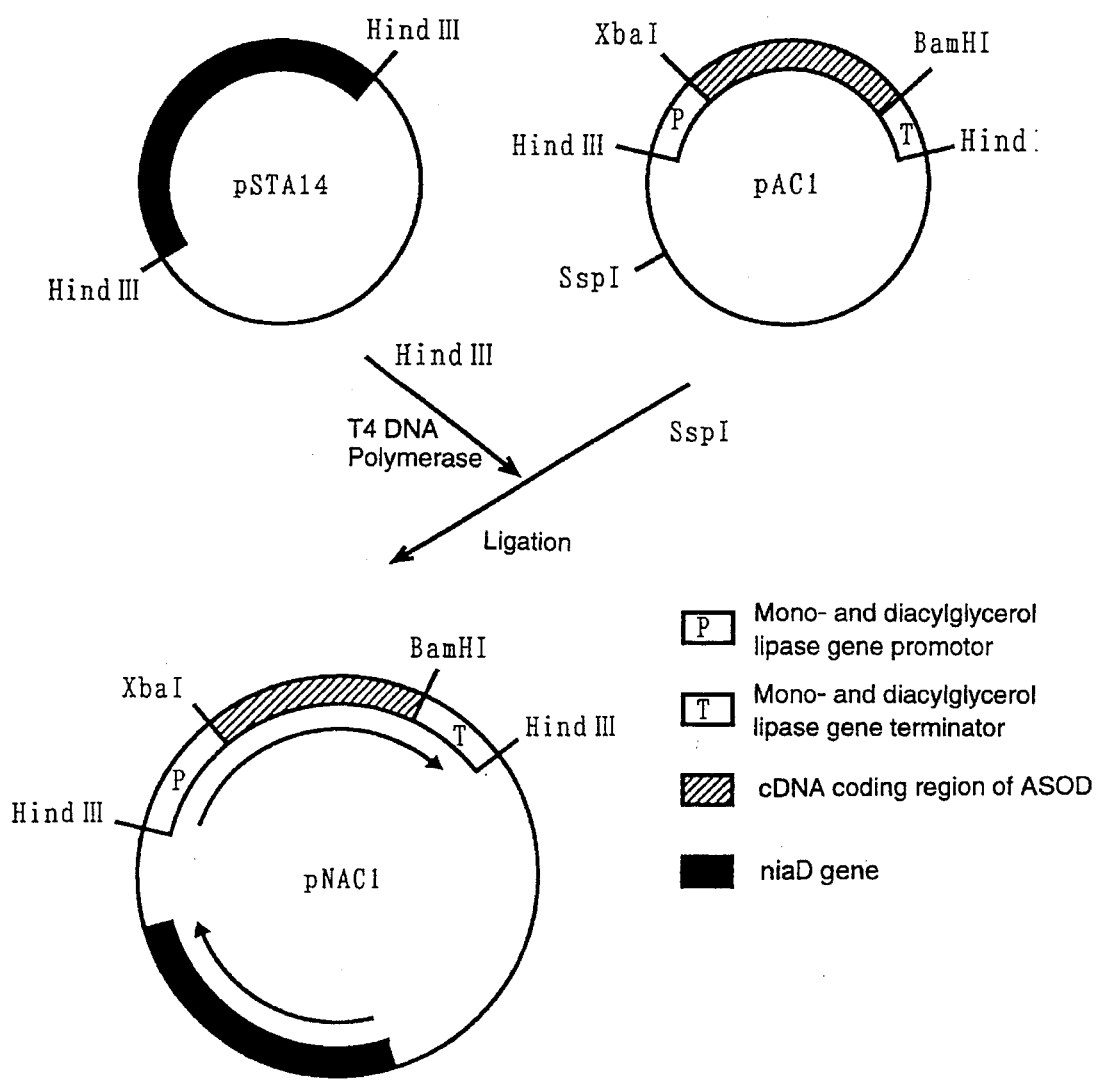
FIG. 11 shows a procedure for the construction of a recombinant plasmid pNAC1.

A transformation plasmid pSTA14 (*Mol. Gen. Genet.*, Vol. 218, pp. 99–104 (1989)) having a niaD gene to be used as a selection marker of *Aspergillus oryzae* was digested with a restriction enzyme HindIII, and the mixture of digested fragments was subjected to 1% low melting point agarose electrophoresis to isolate and purify a DNA fragment of about 5.5 kbp containing the niaD gene. The thus obtained DNA fragment was treated with T4 DNA polymerase to form blunt ends at both termini thereof and then cloned into the SspI restriction enzyme site of the recombinant plasmid pAC1 prepared in Example 5-(11) to obtain a plasmid pNAC1 (FIG. 11).

Using the thus obtained pNAC1, transformation of *Aspergillus oryzae* A01.0 (*Mol. Gen. Genet.*, Vol. 18, pp. 99–104 (1989)) was carried out in accordance with the method of Unkles et al. (*Mol. Gen. Genet.*, Vol. 218, pp. 99–104 (1989)). A transformant grown on a selective medium was cultured in the same manner as described in Example 7.

The ASOD activity in the culture filtrate thus obtained was measured at 2.0 U/ml. When a transformant was isolated using only the selection marker gene-containing plasmid pSTA14 and cultured in the same manner, ASOD activity was not detected.

When each culture filtrate of these transformants was subjected to sugar chain removal in accordance with the procedure described in Example 5-(6) and analyzed by SDS-polyacrylamide gel electrophoresis and western blotting in the same manner as in Example 6, a band of protein having the same molecular weight of native, deglycosylated ASOD was detected only in the case of the pNAC1 transformant, and this protein was confirmed to be capable of reacting with an anti-ASOD antibody.

EXAMPLE 9

Expression of ASOD gene in *Aspergillus niger*

Using the plasmid pHAC1 described in Example 7, transformation of *Aspergillus niger* was carried out in accordance with the method disclosed in JP-A-6-245776. In this case, however, the concentration of hygromycin B in the soft agar to be over-layered was changed to 307.5 μg/ml. A transformant grown on a selective medium was cultured in the same manner as described in Example 7.

When ASOD activity in the culture filtrate thus obtained was measured, the activity was 0.2 U/ml. When a transformant was isolated using only the selection marker gene-containing plasmid pH1 and cultured in the same manner, ASOD activity was not detected.

When each culture filtrate of these transformants was subjected to sugar chain removal in accordance with the procedure described in Example 5-(6) and analyzed by SDS-polyacrylamide gel electrophoresis and western blotting in the similar manner as in Example 6, a band of protein having the same molecular weight of native, deglycosylated ASOD was detected only in the case of the pHAC1 transformant, and this protein was confirmed to be capable of reacting with an antiASOD antibody.

EXAMPLE 10

Expression of ASOD gene in *Eupenicillium brefeldianum*

Figure 12:
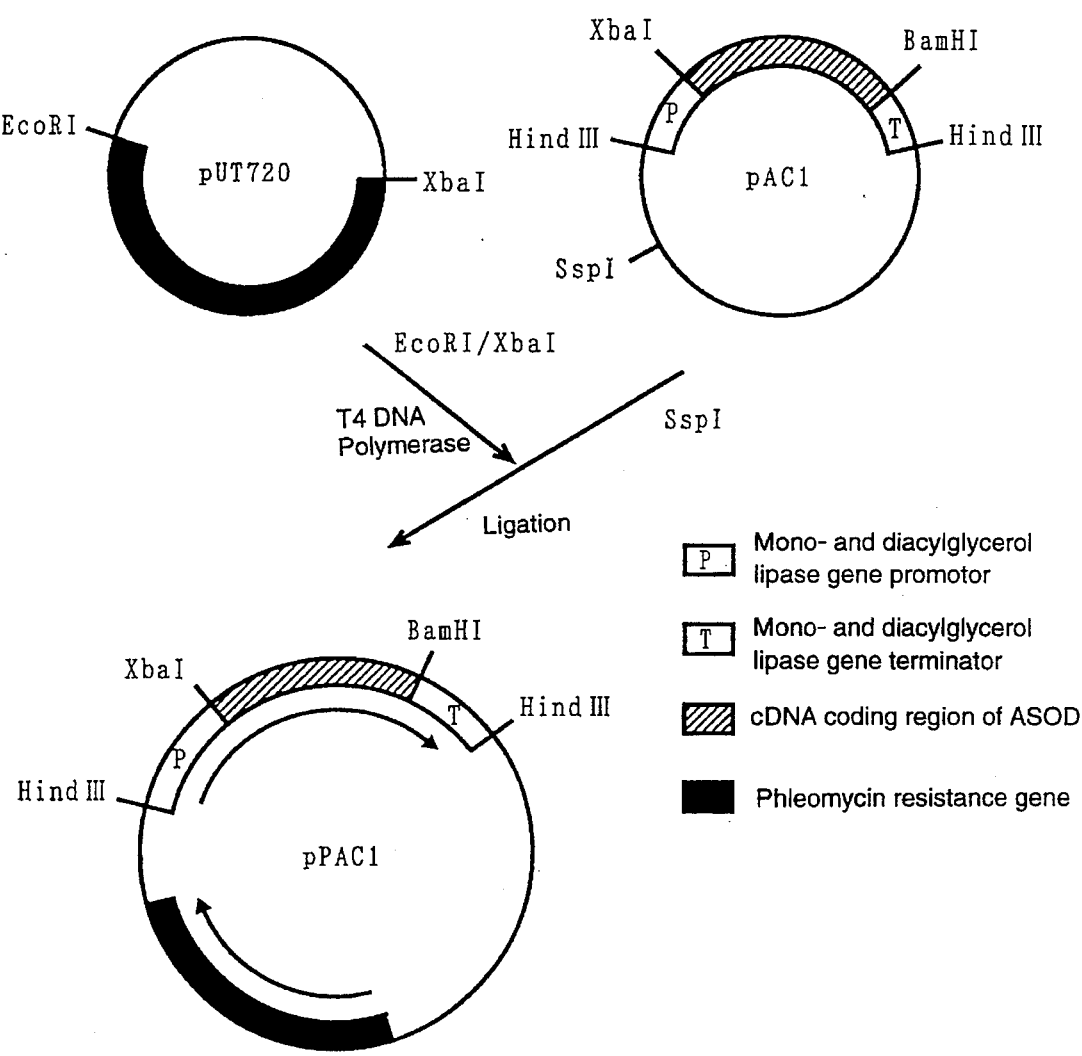
FIG. 12 shows a procedure for the construction of a recombinant plasmid pPAC1.

A transformation plasmid pUT720 (manufactured by CAYLA) having a phleomycin (manufactured by CAYLA) resistance gene to be used as a selection marker of *Eupenicillium brefeldianum* was digested with restriction enzymes EcoRI and XbaI, and the mixture of digested fragments was subjected to 1% low melting point agarose electrophoresis to isolate and purify a DNA fragment of about 3.1 kbp containing the phleomycin resistance gene. The thus obtained DNA fragment was treated with T4 DNA polymerase to form blunt ends at both termini thereof and then cloned into the SspI restriction enzyme site of the recombinant plasmid pAC1 prepared in Example 5-(11) to obtain a plasmid pPAC1 (FIG. 12).

Using the thus obtained plasmid pPAC1, transformation of *Eupenicillium brefeldianum* APC-9315 (FERM BP-5053) was carried out in the following manner.

A 100 μl portion of *Eupenicilliun brefeldianum* spore suspension ($2 \times 10^8$ spores) was inoculated into 100 ml of glucose-peptone medium (manufactured by Eiken Chemical) and cultured at 37° C. for 48 hours with shaking. The resulting cells were collected from the culture by filtration, suspended in 10 ml of a protoplast formation buffer (1.2M sorbitol, 10 mM phosphate buffer, pH 6.0) and then filtered again to collect washed cells.

The washed cells were suspended in the protoplast forming buffer further supplemented with 5 mg/ml of a lysing enzyme (Sigma product number L-2265, manufactured by Sigma), shaken at 30° C. for 2 hours and then filtered with a glass filter 3G2. The resulting filtrate was subjected to 5 minutes of centrifugation at 2,000 rpm. The thus obtained precipitate was suspended in a sorbitol solution (1.2M sorbitol, 50 mM $CaCl_2$, 10 mM Tris-HCl buffer, pH 7.5) and the precipitate was recovered again. By repeating this step again, protoplasts were recovered as a precipitate.

The precipitate was suspended in the sorbitol solution to a protoplast density of $2 \times 10^{8}$/ml. A 50 μl portion of the thus prepared protoplast suspension was mixed with 4 μl of pPAC1 solution (1 μg/μl) and 6.25 μl of a PEG solution (50% PEG 4000, 50 mM $CaCl_2$, 10 mM Tris-HCl buffer, pH 7.5) and then allowed to stand still for 30 minutes in an ice bath. This was mixed with 0.5 ml of the PEG solution and 1 ml of the sorbitol solution in that order.

A 300 μl portion of the resulting mixture was spread on a plate medium consisting of 17 ml of PD (2.4% potato-dextrose broth, manufactured by Difco) and 1.5% agarose, covered with a layer of 3 ml PD containing 0.7% agarose which has been kept at 48° C. in advance, allowed to stand at 30° C. for 24 hours, covered again with 3 ml of PD containing 1.54 mg/ml of phleomycin and 0.7% agarose and then allowed to stand at 30° C. for 4 days. Thereafter, a colony formed on the plate was subcultured on a PD slant medium containing 1.5% agarose and stored as a transformant strain.

The transformant grown on the selective medium was inoculated into 100 ml of 2×glycerol-polypeptone medium (4% glycerol, 6% polypeptone, 0.4% $KH_2PO_4$, 0.02% $MgSO_4.7H_2O$, 0.001% Adecanol, pH 6.0) and cultured at 37° C. for 6 days with shaking.

The ASOD activity in the culture filtrate thus obtained was measured at 18.5 U/ml. When a transformant was isolated using only the selection marker gene-containing plasmid pUT720 and cultured in the same manner, the ASOD activity was found to be 1.8 U/ml.

When each culture filtrate of these transformants was subjected to sugar chain removal in accordance with the procedure described in Example 5-(6) and analyzed by SDS-polyacrylamide gel electrophoresis and western blotting in the similar manner as in Example 6, a band of protein having the same molecular weight of native, deglycosylated ASOD was detected in both cases of the pPAC1 transformant and the control pUT720 transformant, and this protein was confirmed to be capable of reacting with an anti-ASOD antibody. In addition, the pPAC1 transformant showed about a 10 times stronger signal than that of the pUT720 transformant.

EXAMPLE 11

Expression of ASOD gene in *Eupenicillium brefeldianum*

Figure 13:
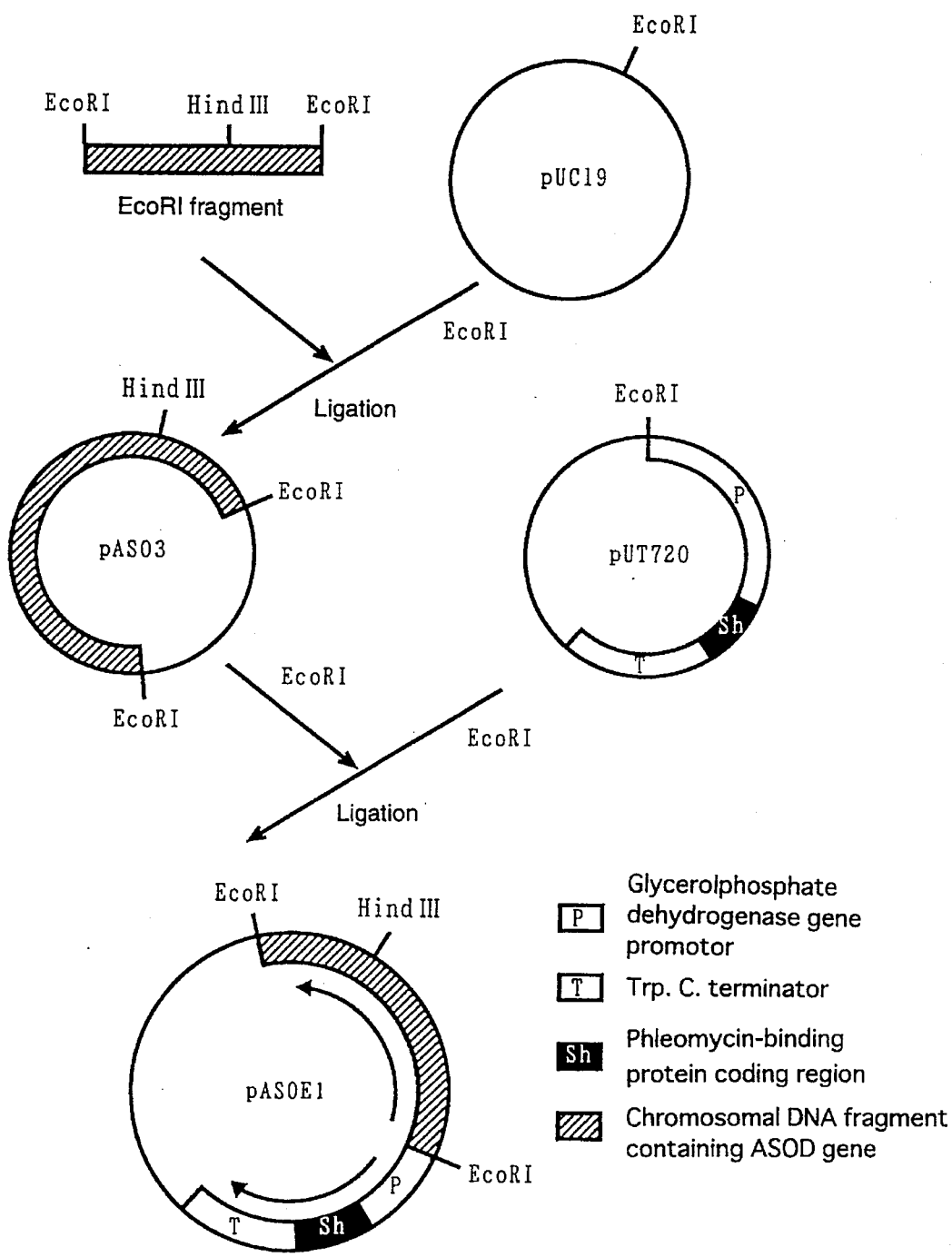
FIG. 13 shows a procedure for the construction of a recombinant plasmid pASOE1.

The pASO3 obtained in Example 5-(9) was digested with EcoRI, and the mixture of digested fragments was subjected to 1% low melting point agarose electrophoresis to isolate and purify a DNA fragment of about 4.2 kbp containing the ASOD gene. The thus obtained DNA fragment was cloned into the EcoRI site of the plasmid pUT720 having a phleomycin resistance gene useful as a selection marker for *Eupenicillium brefeldianum* to obtain a plasmid pASOE1 (FIG. 13).

Using the thus obtained plasmid pASOE1, transformation of *Eupenicillium brefeldianum* APC-9315 was carried out in the same manner as described in Example 10.

Each of the thus obtained transformants showed excellent growth on a medium containing 300 μg/ml of phleomycin, while the parent strain *Eupenicillium brefeldianum* APC-9315 was not able to grow on a medium containing 40 μg/ml or more of phleomycin. The phleomycin resistance of the transformants was stable after 2 isolations of mono spore.

The transformant was cultured in accordance with the procedure of Example 10. When ASOD activity in the culture filtrate thus obtained was measured, the activity was 25.8 U/ml in the case of the transformant having the plasmid pASOE1. When a transformant was isolated using only the selection marker gene-containing plasmid pUT720 and cultured in the same manner, the ASOD activity was found to be 1.4 U/ml.

When each culture filtrate of these transformants was subjected to sugar chain removal in accordance with the procedure described in Example 5-(6) and analyzed by SDS-polyacrylamide gel electrophoresis and western blotting in the similar manner as in Example 6, a band of protein having the same molecular weight of native, deglycosylated ASOD was detected in both cases of the pASOE1 transformant and the control pUT720 transformant, and this protein was confirmed to be capable of undergoing reaction with an anti-ASOD antibody. In addition, the pASOE1 transformant showed about 18 times stronger signal than that of the pUT720 transformant.

EXAMPLE 12

Measurement of Blood Cholesterol

In measuring total cholesterol in serum, the ASOD obtained in Example 2, ASOD obtained in Example 11, or ASO of cucumber origin was added to the assay reagents, and the effect of removing the interfering action of ascorbic acid was examined.

Reagent-1:
 ASOD (or ASO) 3.0 units/ml
 Cholesterol esterase 1.0 unit/ml
 Peroxidase 2.5 units/ml Phenol 1.1 mM PIPES buffer (pH: 6.75) 30 mM Triton X-100 0.1%

Reagent-2:
 Cholesterol oxidase 5.0 units/ml
 Peroxidase 25.0 units/ml
 4-Aminoantipyrine 2.2mM
 PIPES buffer (pH: 6.75 ) 30 mM
 Triton X-100 0.1%

To 10 µl of human control serum (Lipid Serum II, produced by Eiken Kagaku Kabushiki Kaisha) was added 2.25 ml of reagent-1. After incubating at 37° C. for 5 minutes, 0.75 ml of reagent-2 was added, followed by incubation at 37° C. for 5 minutes. The absorbance of the reaction mixture at 500 nm was measured. As a blank, purified water was used in place of human serum.

TABLE 4

| Test Group | $A_{500}$ |
| --- | --- |
| Blank | 0.017 |
| No addition | 0.185 |
| ASO (of cucumber origin) added | 0.215 |
| ASOD (of *E. brefeldianum* APC-9315 origin) added | 0.215 |
| ASOD (prepared in Example 11) added | 0.216 |

As is apparent from Table 4, interference of L-ascorbic acid in the color reaction can be prevented by adding ASOD as well as the conventional ASO of cucumber origin to the reagents. It is apparent that similar results are obtained when recombinant ASOD is used.

EXAMPLE 13

Stability of ASOD-added Reagent

Cholesterol in serum was determined in the same manner as in Example 12, except for using reagent-1 after storage at 37° C. for 20 days (reagent-2 was prepared on use). As can be seen from the results shown in Table 5, the reagent using the ASOD of the present invention is obviously superior in stability to the reagent using ASO of cucumber origin. Similarly, the reagent prepared by using ASOD obtained in Example 11 has superior stability.

TABLE 5

| Test Group | $A_{500}$ Initial | $A_{500}$ Preserved |
| --- | --- | --- |
| Blank | 0.016 | 0.021 |
| No addition | 0.179 | 0.178 |
| ASO (of cucumber origin) added | 0.220 | 0.173 |
| ASOD (of *E. brefeldianum* APC-9315 origin) added | 0.218 | 0.220 |
| ASOD (prepared in Example 11) added | 0.219 | 0.218 |

EXAMPLE 14

Measurement of Blood Triglyceride

In measuring triglyceride in serum, the ASOD obtained in Example 2 was added to the reagents, and the effect of removing the interfering action of ascorbic acid was examined.

Reagent-1:
 Glycerol kinase 7 U/ml
 Glycerol-3-phosphate oxidase 22 U/ml
 Peroxidase 2 U/ml
 ASOD 2 U/ml
 TOOS (N-Ethyl-N-(2-hydroxy-3-sulfopropyl)-methylaniline) 1.5mM
 ATP 3 mM
 Magnesium acetate 10 mM
 EDTA.2Na 1 mM
 Surface active agent 0.1%
 Sodium azide 0.02%
 Sodium dehydroacetate 0.02%
 PIPES.NaOH buffer (pH: 6.6) 20 mM Reagent-2:
 Lipoprotein lipase 600 U/ml
 Peroxidase 12 U/ml
 4-Aminoantipyrine 3 mM
 EDTA-2Na 1 mM
 Surface active agent 0.1%
 Sodium azide 0.02%
 Sodium dehydroacetate 0.02%
 PIPES.NaOH buffer (pH: 6.6) 70 mM To 27 µl of human control serum (Lipid Serum II, produced by Eiken Kagaku Kabushiki Kaisha) were added 3 µl of L-ascorbic acid (50 mg/ml) and 2.25 ml of reagent-1. After incubating at 37° C. for 5 minutes, 0.75 ml of reagent-2 was added, followed by incubation at 37° C. for 5 minutes. The absorbance of the reaction mixture at 555 nm was measured. As a control, purified water was used in place of L-ascorbic acid.

TABLE 6

| L-Ascorbic Acid | ASOD | $A_{555}$ |
| --- | --- | --- |
| added | added | 0.179 |
| added | not added | 0.060 |
| not added | added | 0.185 |
| not added | not added | 0.186 |

It is apparent from Table 6 that interference of ascorbic acid in coloring reaction can be prevented by the ASOD of the present invention. It is found that hydrogen peroxide produced by oxidation of L-ascorbic acid by the action of the ASOD gives no influence on the measurement. Similarly, it was also confirmed that the measured value is not influenced when a reagent prepared by using ASOD obtained in Example 11 was used.

EXAMPLE 15

Quantitative Determination of L-Ascorbic Acid

To 10 µl of a 20 mM acetic acid-sodium acetate buffer (pH: 4.0) containing L-ascorbic acid of varying concentration were added 40 µl (0.5 U) of the ASOD of the present invention, and the mixture was allowed to react at 37° C. for 10 minutes to completely convert L-ascorbic acid to dehydroascorbic acid.

To the reaction mixture was added 2.95 ml of a 100 mM phosphate buffer (pH: 7.0) containing 3 mM 4-aminoantipyrine, 1 mM phenol, and 8 U/ml peroxidase, followed by reacting at 37° C. for 5 minutes. The amount of hydrogen peroxide produced by oxidation of L-ascorbic acid was determined by measuring the absorbance of the dye formed on oxidative condensation of 4-aminoantipyrine and phenol at 505 nm. The results obtained are shown in FIG. 14, in which the abscissa indicates L-ascorbic acid (ASA) concentration (mM), and the ordinate indicates the absorbance at 505 nm.

Figure 14:
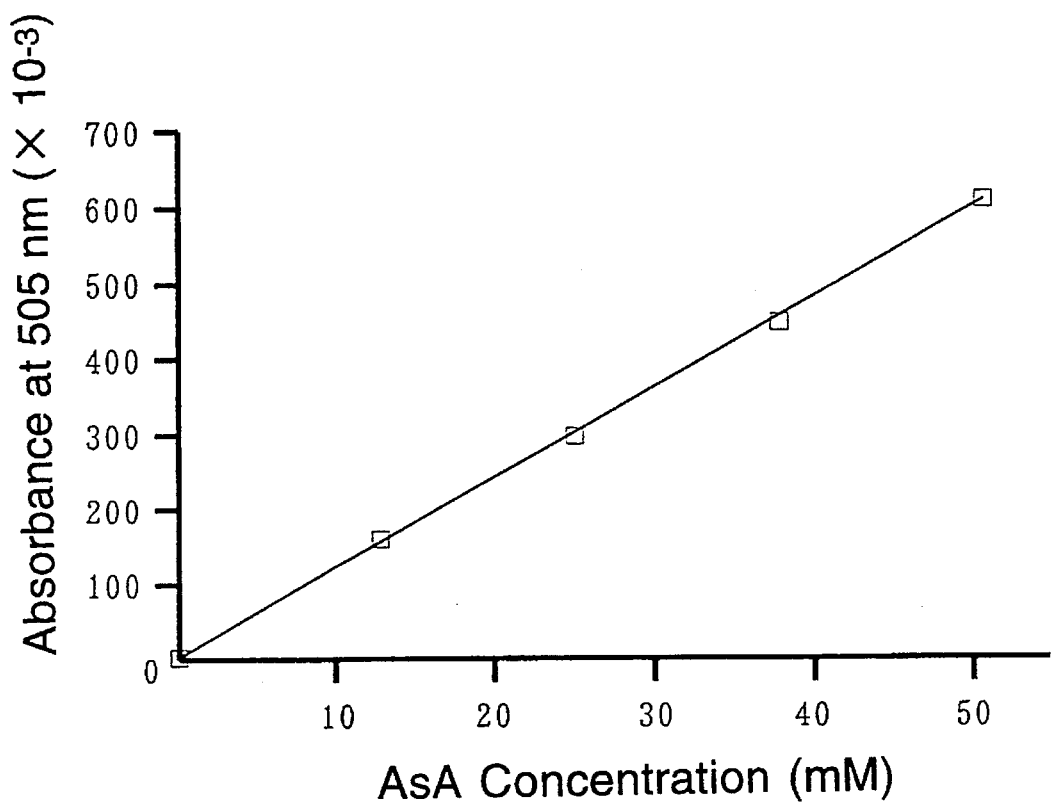
FIG. 14 is a calibration curve for L-ascorbic acid.

It is apparent from FIG. 14 that the amount of L-ascorbic acid in a sample can be precisely determined by making use of the direct proportional relationship (linear relationship) between the L-ascorbic acid content and the absorbance. The same results were obtained when the enzyme obtained in Example 11 was used.

EXAMPLE 16

Quantitative Determination of Ascorbic Acid in Food

The L-ascorbic acid content in lemon juice was measured in the same manner as in Example 15. At the same time, the measurement was made by the hydrazine colorimetry method to obtain a comparative result.

As a result, the ascorbic acid content in 100 ml of lemon juice was found to be 37.0 mg (calculated from the calibration curve of Example 15) according to the method of the present invention, whereas it was 35.9 mg according to the hydrazine colorimetry method [(total ascorbic acid)-(dehydroascorbic acid)]. It is thus apparent that an L-ascorbic acid content in foods can be measured satisfactorily by using the ASOD of the present invention. The same results were obtained when the enzyme obtained in Example 11 was used.

EXAMPLE 17

With respect to the enzymes derived from microorganisms other than Eupenicillium (Table 1) and the recombinant enzymes obtained in Example 4 to 11, various measurements were conducted in the same manner as in Examples 12 to 16. As a result, similar results were obtained.

According to the present invention, there is provided a novel ASOD and a gene encoding ASOD. By culturing the transformant in which the gene is integrated, it is possible to produce the ASOD in high volume in an inexpensive way. When known ASO is used in reagents for clinical examination for removal of interfering substances, the instability of the ASO, particularly in liquid reagents, has made it inevitable to use various stabilizers in combination therewith and also to add ASO in excess so as to make up for the deactivation during storage. Use of the ASOD of the present invention excludes the necessity of adding stabilizers and adding an extra amount of ASOD. That is, the advantages of the ASOD according to the present invention over conventional ASO, i.e., very high stability, not inhibited by sodium azide, and the optimum pH in the vicinity of neutrality, make it possible to reduce the required amount of the enzyme to be added to a reagent for clinical examination, which ultimately leads to reduction of cost and avoidance of influences of impurities.

While the invention has been described in detail and with reference to specific examples thereof, it will be apparent to one skilled in the art that various changes and modifications can be made therein without departing from the spirit and scope thereof.

---

What is claimed is:

1. An isolated ascorbate oxidase obtained from a strain belonging to the genus Eupenicillium which has a residual activity of at least 50% when stored at 37° C. for one month in a buffer comprising 50 piperazine-N,N'-bis (2-ethanesulfonic acid (PIPES) (pH 6.5), 0.02M dehydroacetic acid and 1 mM ethylenediaminetetraacetic acid (EDTA) and catalyzes reaction of one molecule of L-ascorbic acid and one molecule of molecular oxygen to form one molecule of L-dehydroascorbic acid and one molecule of hydrogen peroxide.

2. A process for producing an ascotbate oxidase which catalyzes oxidation of L-ascorbic acid and produces as a product hydrogen peroxide comprising culturing a strain belonging to the genus Eupenicillium to produce said ascorbate oxidase and harvesting the ascorbate oxidase produced.

3. A gene encoding ascorbate oxidase obtained from a strain belonging to the genus Eupenicillium which has a SacI-SalI-Eco47III-SalI-KpnI-HindIII-BstEII restriction enzyme map as set forth in FIG. 6, wherein the amino terminal valine of said ascorbate oxidase is encoded by the SalI restriction site denoted by an asterisk in FIG. 6.

4. A transformant containing a DNA fragment comprising a gene encoding ascotbate oxidase obtained from a strain belonging to the genus Eupenicillium which has a SacI-SalI-Eco47III-SalI-KpnI-HindIII-BstEII restriction enzyme map as set forth in FIG. 6, wherein the amino terminal valine of said ascorbate oxidase is encoded by the SalI restriction site denoted by an asterisk in FIG. 6 and a DNA fragment which promotes expression of said gens.

5. A process for producing an ascotbate oxidase obtained from a strain belonging to the genus Eupenicillium which comprising a culturing a eukaryotic transformant containing a DNA fragment comprising a gene encoding ascorbate oxidase which has a SacI-SalIEco47III-SalI-KpnI-HindIII-BstEII restriction enzyme map as set forth in FIG. 6, wherein the amino terminal valine of said ascorbate oxidase is encoded by the SalI restriction site denoted by an asterisk in FIG. 6 and a DNA fragment which promotes expression of said gene, and harvesting the ascotbate oxidase from the culture.

6. A cDNA fragment encoding ascorbate oxidase obtained from a strain belonging to the genus Eupenicillium which has a restriction enzyme map as set forth in FIG. 7.

7. A transformant containing a DNA fragment comprising a cDNA fragment encoding ascotbate oxidase obtained from a strain belonging to the genus Eupenicillium which has a restriction enzyme map as set forth in FIG. 7 and a DNA fragment which promotes expression of said gene.

8. A process for producing an ascorbate oxidase obtained from a strain belonging to the genus Eupenicillium comprising culturing a transformant containing a DNA fragment comprising a cDNA fragment encoding ascorbate oxidase which has a restriction enzyme map as set forth in FIG. 7 and a DNA fragment which promotes expression of said gene, and harvesting the ascorbate oxidase from the culture.

9. The process for producing an ascorbate oxidase according to claim 5 or 8, wherein said transformant is a microorganism belonging to the genus Saccharomyces, Penicillium, Aspergillus, or Eupenicillium.

10. A reagent composition comprising an ascotbate oxidase obtained from a strain belonging to the genus Eupenicillium which has a residual activity of at least 50% when stored at 37° C. for one month in a buffer comprising 50 mM piperazine-N,N'-bis(2-ethanesulfonic acid (PIPES) (pH 6.5), 0.02M dehydroacetic acid and 1 mM ethylenediaminetetraacetic acid (EDTA) and catalyzes the reaction of L-ascorbic acid and molecular oxygen to form L-dehydroascorbic acid and hydrogen peroxide, and a carrier, excipient or diluent.

11. A food composition comprising an ascorbate oxidase obtained from a strain belonging to the genus Eupenicillium which has a residual activity of at least 50% when stored at 37° C. for one month in a buffer comprising 50 mM piperazine-N,N'-bis(2-ethanesulfonic acid (PIPES) (pH 6.5), 0.02M dehydroacetic acid and 1 mM ethylenediaminetetraacetic acid (EDTA) and catalyzes the reaction of L-ascorbic acid and molecular oxygen to form L-dehydroascorbic acid and hydrogen peroxide, and a food.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Eupenicillium brefeldianum
        ( B ) STRAIN: APC-9315

( x i ) SEQUENCE DESCRIPTION: SEQ ID NO:1:

```
Val  Asp  Pro  Ala  Ala  Val  Tyr  Asn  Gly  Gly  Tyr  Asn  Ser  Thr  Lys  Asn
1              5                        10                          15

Val  Ala  Leu  Arg
               20
```

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
    ( A ) ORGANISM: Eupenicillium brefeldianum
    ( B ) STRAIN: APC-9315

( x i ) SEQUENCE DESCRIPTION: SEQ ID NO:2:

```
Gly Ile Ala Lys Ser Pro Ala Trp Tyr Thr Trp Arg Asp His Phe Leu
1               5                   10                  15

Leu Val Gly Pro
            20
```

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( B ) STRAIN: Eupenicillium brefeldianum
        ( C ) INDIVIDUAL ISOLATE: APC- 9315

( x i ) SEQUENCE DESCRIPTION: SEQ ID NO:3:

```
Phe Thr Gln Trp Ala Ile Ser Ala Glu Gly Gln Lys
1               5                   10
```

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( B ) STRAIN: Eupenicillium brefeldianum
        ( C ) INDIVIDUAL ISOLATE: APC- 9315

( x i ) SEQUENCE DESCRIPTION: SEQ ID NO:4:

```
Asn Gly Ser Asp Pro Phe Glu Val Ala Trp Tyr Lys
1               5                   10
```

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: Not Relevant
        ( D ) TOPOLOGY: linear ( i i ) MOLECULE TYPE: DNA (genomic)

( v i ) ORIGINAL SOURCE:
        ( A ) ORGANISM: Eupenicillium brefeldianum
        ( B ) STRAIN: APC-9315

( i x ) FEATURE:
        ( A ) NAME/KEY: CDS
        ( B ) LOCATION: 1..30

( x i ) SEQUENCE DESCRIPTION: SEQ ID NO:5:

```
GTC GAC CCT GCT GCC GTC TAC AAT GGA GGG                              30
Val Asp Pro Ala Ala Val Tyr Asn Gly Gly
1               5                   10
```

( 2 ) INFORMATION FOR SEQ ID NO:6:

( i ) SEQUENCE CHARACTERISTICS:
   ( A ) LENGTH: 10 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:6:

Val Asp Pro Ala Ala Val Tyr Asn Gly Gly
 1               5                   10

( 2 ) INFORMATION FOR SEQ ID NO:7:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc ="Synthetic DNA"

( i v ) ANTI-SENSE: NO ( i x ) FEATURE:
      ( A ) NAME/KEY: modified_base
      ( B ) LOCATION: 6
      ( D ) OTHER INFORMATION: /mod_base=i ( i x ) FEATURE:
      ( A ) NAME/KEY: modified_base
      ( B ) LOCATION: 12
      ( D ) OTHER INFORMATION: /mod_base=i ( x i ) SEQUENCE DESCRIPTION: SEQ ID NO:7:

CCNGCNGCNG TNTA Y AA Y GG NGG                                                   23

( 2 ) INFORMATION FOR SEQ ID NO:8:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc ="Synthetic DNA"

( i v ) ANTI-SENSE: YES ( i x ) FEATURE:
      ( A ) NAME/KEY: modified_base
      ( B ) LOCATION: 3
      ( D ) OTHER INFORMATION: /mod_base=i ( i x ) FEATURE:
      ( A ) NAME/KEY: modified_base
      ( B ) LOCATION: 9
      ( D ) OTHER INFORMATION: /mod_base=i ( i x ) FEATURE:
      ( A ) NAME/KEY: modified_base
      ( B ) LOCATION: 18
      ( D ) OTHER INFORMATION: /mod_base=i ( x i ) SEQUENCE DESCRIPTION: SEQ ID NO:8:

TCNCKTCANG TRTACCANGC NGG                                                       23

( 2 ) INFORMATION FOR SEQ ID NO:9:

( i ) SEQUENCE CHARACTERISTICS:
      ( A ) LENGTH: 30 base pairs
      ( B ) TYPE: nucleic acid
      ( C ) STRANDEDNESS: single (D) TOPOLOGY: linear (ii) MOLECULE TYPE: other nucleic acid
    (A) DESCRIPTION: /desc ="Synthetic DNA"

(iv) ANTI-SENSE: NO (xi) SEQUENCE DESCRIPTION: SEQ ID NO:9:

ATTCTAGACA TCATGCGTTC CTATACTTTG                 30

(2) INFORMATION FOR SEQ ID NO:10:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc ="Synthetic DNA"

(iv) ANTI-SENSE: YES (xi) SEQUENCE DESCRIPTION: SEQ ID NO:10:

GTGGATCCTA TCAACAACAC TCGGTTGC                   28